(12) United States Patent
Kitano et al.

(10) Patent No.: US 8,540,622 B2
(45) Date of Patent: Sep. 24, 2013

(54) ENDOSCOPE

(75) Inventors: Seiji Kitano, Kodaira (JP); Takashi Otawara, Hachioji (JP); Takayasu Miyagi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 97 days.

(21) Appl. No.: 13/248,433

(22) Filed: Sep. 29, 2011

(65) Prior Publication Data

US 2012/0078041 A1 Mar. 29, 2012

Related U.S. Application Data

(63) Continuation of application No. PCT/JP2011/061743, filed on May 23, 2011.

(30) Foreign Application Priority Data

May 28, 2010 (JP) ................................ 2010-123501

(51) Int. Cl.
*A61B 1/00* (2006.01)

(52) U.S. Cl.
USPC ............ 600/107; 600/104; 600/106; 600/129

(58) Field of Classification Search
USPC ................................................ 600/106–107
See application file for complete search history.

(56) References Cited

U.S. PATENT DOCUMENTS

| | | | | |
|---|---|---|---|---|
| 4,407,273 | A | * | 10/1983 | Ouchi ............................ 600/107 |
| 7,341,555 | B2 | * | 3/2008 | Ootawara et al. ............. 600/106 |
| 2002/0091303 | A1 | | 7/2002 | Ootawara |
| 2004/0049095 | A1 | | 3/2004 | Goto et al. |
| 2007/0197871 | A1 | * | 8/2007 | Geitz et al. .................... 600/117 |
| 2007/0249898 | A1 | | 10/2007 | Otawara |
| 2007/0270638 | A1 | | 11/2007 | Kitano et al. |
| 2009/0054727 | A1 | | 2/2009 | Yamaya |

FOREIGN PATENT DOCUMENTS

| | | |
|---|---|---|
| EP | 1 764 028 A1 | 3/2007 |
| EP | 1 857 039 A2 | 11/2007 |
| JP | 61-53496 U | 10/1987 |

(Continued)

OTHER PUBLICATIONS

European Search Report dated May 3, 2012 from corresponding European Patent Application No. EP 11 78 6593.1.

*Primary Examiner* — Matthew J Kasztejna
(74) *Attorney, Agent, or Firm* — Scully, Scott, Murphy & Presser, P.C.

(57) ABSTRACT

An endoscope includes: a distal end opening of a treatment instrument insertion channel opened at a side surface of a distal end portion; a treatment instrument elevator base that is provided at a position facing the distal end opening in the treatment instrument insertion channel and leads a distal end of a treatment instrument protruding from the distal end opening, to a desired position; a first wall portion along the insertion direction of the distal end opening; and a second wall portion at a proximal end side of the insertion direction of the distal end opening and provided with a groove in which a part of the treatment instrument elevator base is fitted when the treatment instrument elevator base is raised, and as the treatment instrument elevator base is raised, a guide wire protruding from the distal end opening is releasably engaged by contacting the treatment instrument elevator base, the first wall portion, and a surface constituting the groove of the second wall portion.

7 Claims, 19 Drawing Sheets

(56) References Cited

FOREIGN PATENT DOCUMENTS

| | | |
|---|---|---|
| JP | 2002-34905 A | 2/2002 |
| JP | 2003-305002 A | 10/2003 |
| JP | 2006-15017 A | 1/2006 |
| JP | 2006-20725 A | 1/2006 |
| JP | 2006-280602 A | 10/2006 |
| JP | 2007-307086 A | 11/2007 |
| JP | 2007-330756 A | 12/2007 |
| WO | WO 01/78581 A1 | 10/2001 |
| WO | WO 2006/106881 A1 | 10/2006 |

* cited by examiner

ENDOSCOPE

CROSS REFERENCE TO RELATED APPLICATION

This application is a continuation application of PCT/JP2011/061743 filed on May 23, 2011 and claims benefit of Japanese Application No. 2010-123501 filed in Japan on May 28, 2010, the entire contents of which are incorporated herein by this reference.

BACKGROUND OF THE INVENTION

1. Field of the Invention

The present invention relates to an endoscope in which a distal end opening of a treatment instrument insertion channel provided in an insertion portion to be inserted into a subject is formed at a side surface of the insertion portion, and a treatment instrument elevator base is provided at a position facing the distal end opening of the treatment instrument insertion channel.

2. Description of the Related Art

In recent years, an endoscope having an observation optical system on a side of a distal end portion at a distal end side of an insertion portion of the endoscope in an insertion direction (hereinafter, simply referred to as the distal end side), what is called a side-view type endoscope, has been used to treat a disorder region in a digestive tract system, a pancreaticobiliary duct system, and the like.

Examples of treatments of pancreaticobiliary duct systems or the like using the side-view type endoscope include a diagnostic treatment for endoscopically imaging a bile duct or a pancreatic duct using an endoscope as well as a therapeutic treatment for collecting a bile stone existing in a choledoch duct or the like by a balloon or a gripping treatment instrument.

Furthermore, in the endoscope treatment for a pancreatic duct, a bile duct, a hepatic duct, or the like, since the pancreatic, the bile, and the hepatic ducts are extremely thin, it is challenging to insert a distal end portion of an insertion portion of an endoscope directly into such a duct.

Thus, in general, a distal end portion of an insertion portion of a side-view type endoscope is inserted to the vicinity of the duodenal papilla, and from there, under X-ray fluoroscopy, a guide wire protruding from a distal end opening of a treatment instrument insertion channel in an insertion portion is inserted into the foregoing ducts, the channel being formed in a side surface of the distal end portion of the insertion portion, and a treatment instrument such as a catheter is then selectively inserted into the pancreatic duct, the bile duct, or the hepatic duct with the guide wire as a guide.

According to the technique, once a guide wire is inserted into a pancreatic duct, a bile duct, or a hepatic duct, which is thin, treatment instruments can be inserted into and withdrawn from the duct through the guide wire repeatedly.

A guide wire or a treatment instrument is inserted into the duct through a distal end opening, in a treatment instrument insertion channel, by raising a known treatment instrument elevator base provided at a position facing the distal end opening.

Japanese Patent Application Laid-Open Publication Nos. 2002-34905 and 2003-305002 propose a technique with which when a treatment instrument is withdrawn from a pancreatic duct, a bile duct, or a hepatic duct, after the treatment instrument is withdrawn by raising a treatment instrument elevator base, from the foregoing ducts to a proximal end side in an insertion direction of an insertion portion (hereinafter, simply referred to as the proximal end side) with respect to a position at which the guide wire is bent, the treatment instrument elevator base is further raised, and thereby the guide wire is further raised to be retained between the treatment instrument elevator base and an insulating member at a proximal end side of a distal end opening to fix a position of the guide wire.

Specifically, Japanese Patent Application Laid-Open Publication No. 2002-34905 discloses a configuration in which on a guide plane that leads a guide wire or a treatment instrument on a treatment instrument elevator base, a substantially V-shaped or U-shaped groove in section is formed at a substantially center part of a planar view of the guide plane, and in a state where the guide wire is engaged in the groove, namely, a state where the guide wire is engaged in a center part of the guide plane, a treatment instrument elevator base is raised, and thereby the guide wire is retained and fixed between an insulating member and the groove in the treatment instrument elevator base in a shearing manner (hereinafter, referred to as the center lock configuration, and fixation of a guide wire at a center part of a guide plane is referred to as the center lock).

Furthermore, Japanese Patent Application Laid-Open Publication No. 2003-305002 discloses a configuration in which in a distal end opening, a treatment instrument elevator base is raised with a guide wire tilted toward a side of an observation optical system side provided with the distal end opening on a side surface of the distal end portion of the insertion portion, and thereby between an edge at a side close to the observation optical system of the treatment instrument elevator base and a run off portion of the close-side edge formed in an insulating member, the guide wire is more firmly retained and fixed than the center lock configuration by an edge surface and a surface of the run off portion (hereinafter, referred to as the side lock configuration, and fixation of a guide wire with the guide wire tilted toward the observation optical system side of the distal end opening is referred to as the side lock).

In general, since a guide wire is fixed within the scope of field of view of an observation optical system, the endoscope having the center lock configuration described in Japanese Patent Application Laid-Open Publication No. 2002-34905 or the side lock configuration described in Japanese Patent Application Laid-Open Publication No. 2003-305002 is sufficient.

However, although less frequently, an operator may experience a situation where in some cases, in a distal end opening, a guide wire has to be fixed with the guide wire tilted to a direction spaced apart from the observation optical system, the direction being out of the field of view of the observation optical system (for example, in a state where a guide wire cannot be led to a side lock configuration side, the guide wire must be fixed).

In view of such circumstances, similarly to the side lock configuration described in Japanese Patent Application Laid-Open Publication No. 2003-305002, by retaining a guide wire between a surface of an edge at a side spaced apart from an observation optical system of the treatment instrument elevator base and a surface of a run off portion of the spaced-side edge formed on an insulating member, the guide wire may be fixed with the guide wire tilted toward the side spaced apart from the observation optical system.

SUMMARY OF THE INVENTION

An endoscope according to an aspect of the present invention includes: a distal end opening of a treatment instrument insertion channel provided in an insertion portion inserted into a subject, the opening being made at a side surface of a distal end portion at a distal end side of an insertion direction of the insertion portion; a treatment instrument elevator base that is, in the distal end portion, provided at a position facing the distal end opening in the treatment instrument insertion channel and leads a distal end of a treatment instrument protruding from the distal end opening, to a desired position; a first wall portion along the insertion direction of the distal end opening; and a second wall portion at a proximal end side of the insertion direction of the distal end opening and provided with a groove in which a part of the treatment instrument elevator base is fitted when the treatment instrument elevator base is raised, and as the treatment instrument elevator base is raised, a guide wire protruding from the distal end opening is releasably engaged by contacting the treatment instrument elevator base, the first wall portion, and a surface constituting the groove of the second wall portion.

DETAILED DESCRIPTION OF THE PREFERRED EMBODIMENT

Hereinafter, an embodiment of the present invention will be described with reference to the drawings. It should be noted that the drawings are schematic representations, so that a relationship between a thickness and a width of each member and a thickness ratio of each member are different from actual ones. It is needless to say that there are parts with dimensional relationships and ratios different between the drawings.

Figure 1:
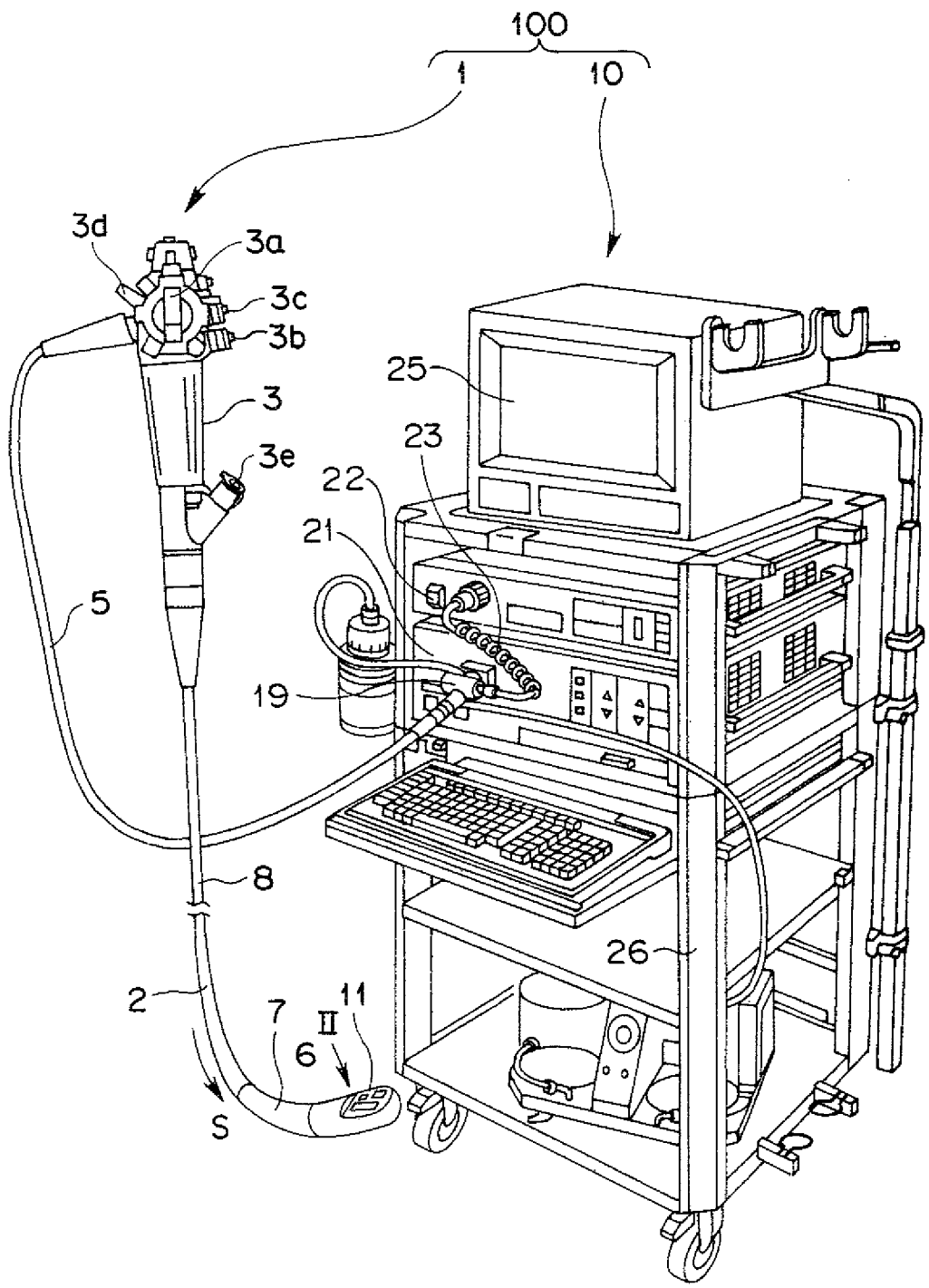
FIG. 1 is an external perspective view of an endoscope apparatus viewed from the front right upper side and showing the present embodiment, the apparatus being composed of an endoscope and a peripheral device.
Figure 2:
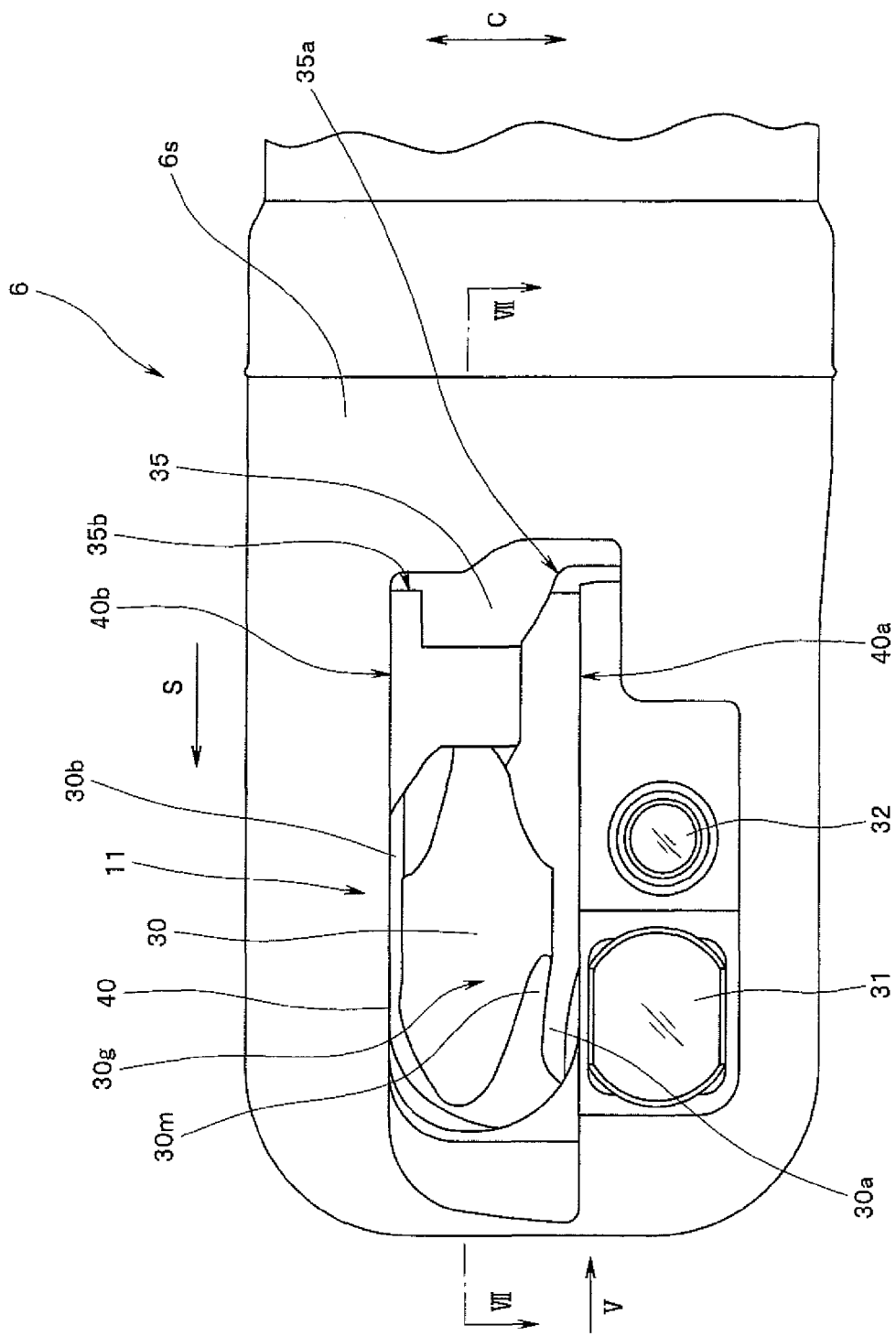
FIG. 2 is a partial enlarged plan view of a distal end portion of an insertion portion of FIG. 1 as viewed from a II direction in FIG. 1.

FIG. 1 is an external perspective view of an endoscope apparatus viewed from the front right upper side and showing the present embodiment, the apparatus being composed of an endoscope and a peripheral device. FIG. 2 is a partial enlarged plan view of a distal end portion of an insertion portion of FIG. 1 as viewed from a II direction in FIG. 1.

Figure 3:
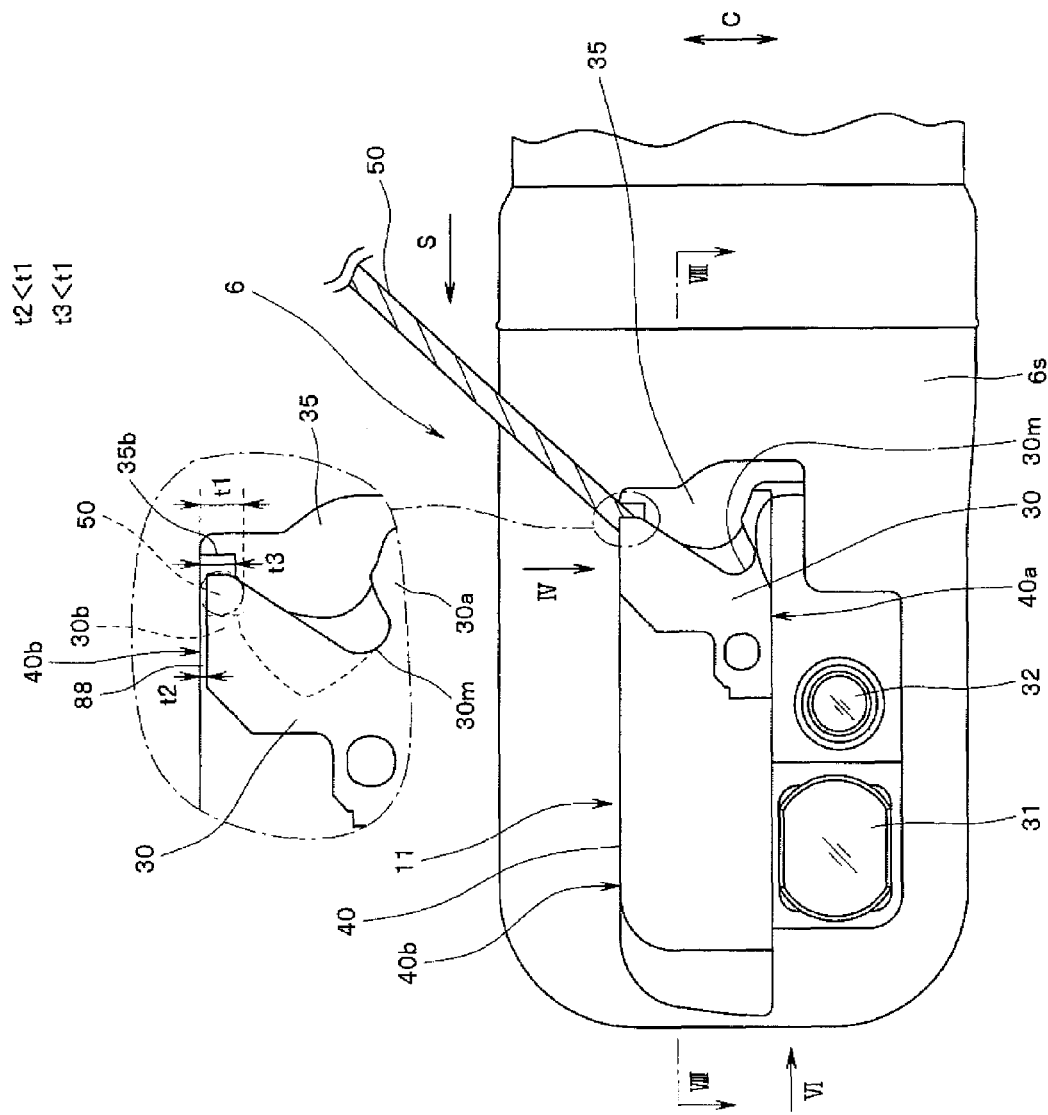
FIG. 3 is a partial enlarged plan view schematically showing a state in which a treatment instrument elevator base provided in a distal end opening of FIG. 2 is raised to fix a position of a guide wire.
Figure 4:
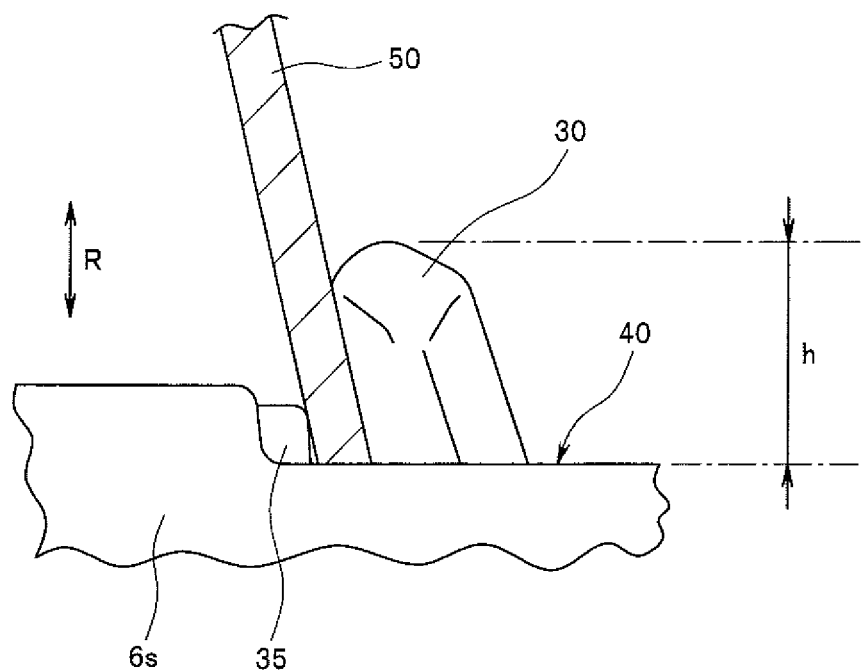
FIG. 4 is a partial enlarged view of a fixation portion for the guide wire in FIG. 3 as viewed from a IV direction in FIG. 3.

Further, FIG. 3 is a partial enlarged plan view schematically showing a state in which a treatment instrument elevator base provided in a distal end opening of FIG. 2 is raised to fix a position of a guide wire. FIG. 4 is a partial enlarged view of a fixation portion for the guide wire in FIG. 3 as viewed from a IV direction in FIG. 3.

Figure 5:
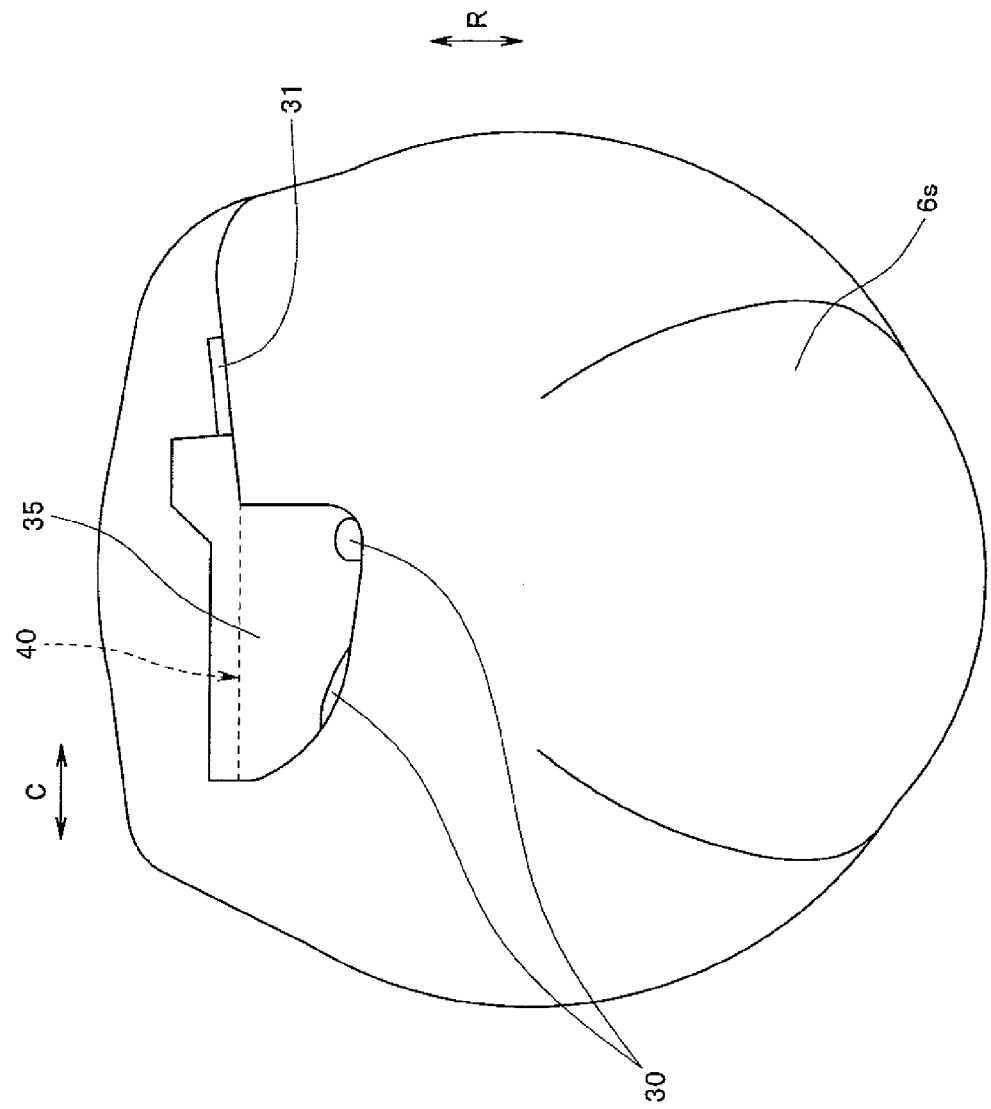
FIG. 5 is a diagram of the distal end portion of the insertion portion in FIG. 2 as viewed from a V direction in FIG. 2.
Figure 6:
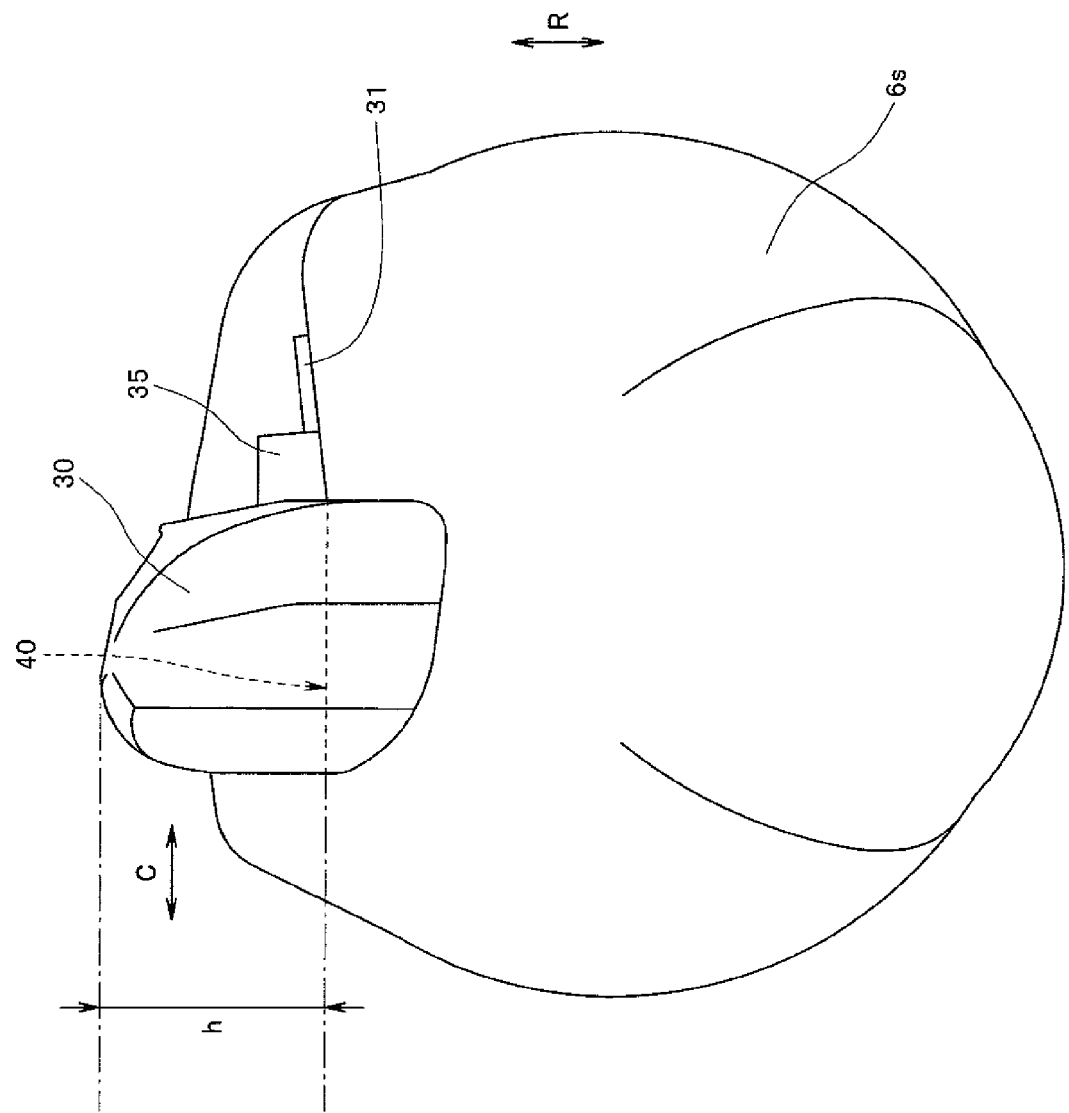
FIG. 6 is a diagram of the distal end portion of the insertion portion in FIG. 3 as viewed from a VI direction in FIG. 3.
Figure 7:
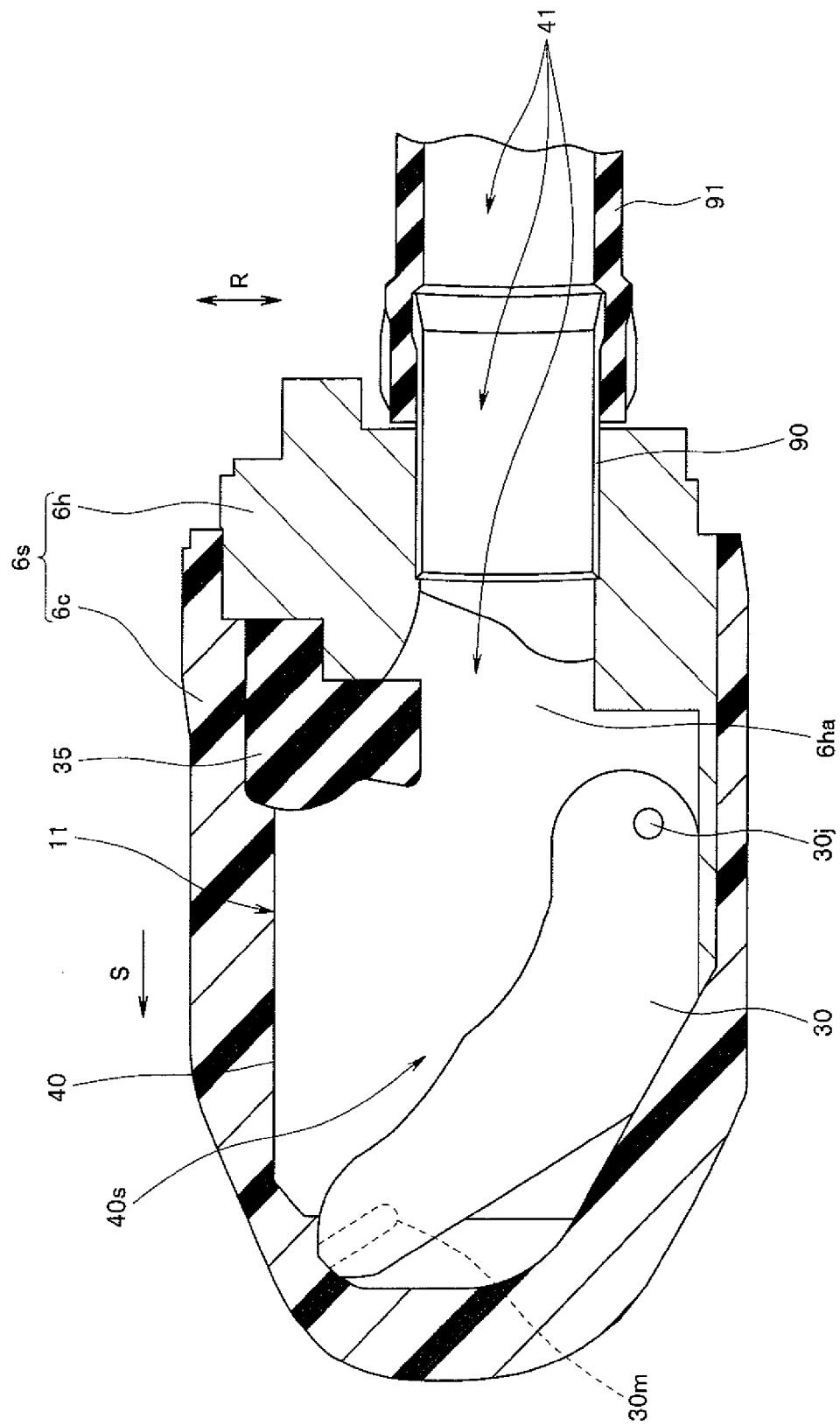
FIG. 7 is a partial cross-sectional view of the distal end portion of the insertion portion, taken along a line VII-VII in FIG. 2.
Figure 8:
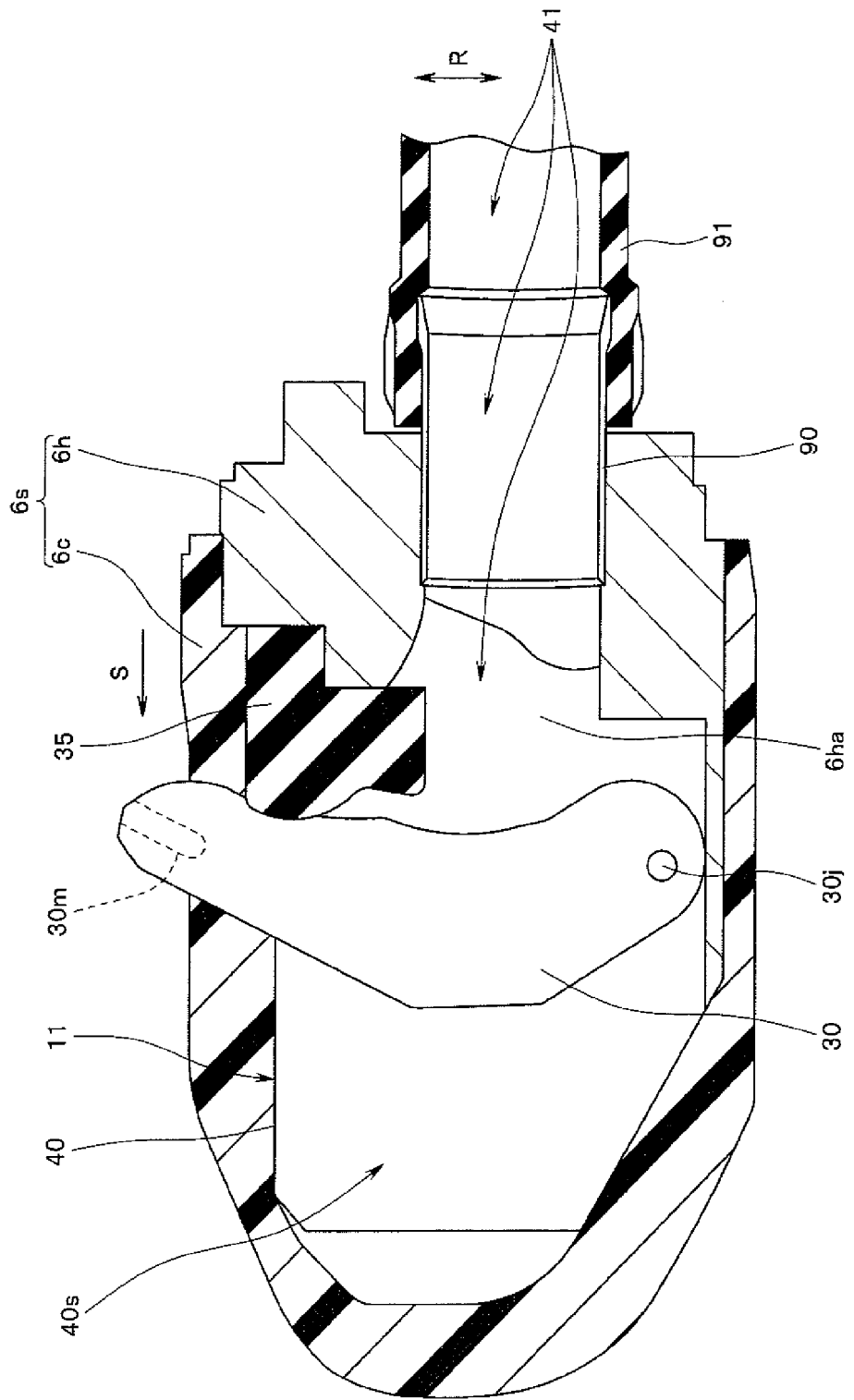
FIG. 8 is a partial cross-sectional view of the distal end portion of the insertion portion, taken along a line VIII-VIII in FIG. 3.

Further, FIG. 5 is a diagram of the distal end portion of the insertion portion in FIG. 2 as viewed from a V direction in FIG. 2. FIG. 6 is a diagram of the distal end portion of the insertion portion in FIG. 3 as viewed from a VI direction in FIG. 3. FIG. 7 is a partial cross-sectional view of the distal end portion of the insertion portion, taken along a line VII-VII in FIG. 2. FIG. 8 is a partial cross-sectional view of the distal end portion of the insertion portion, taken along a line VIII-VIII in FIG. 3.

Figure 9:
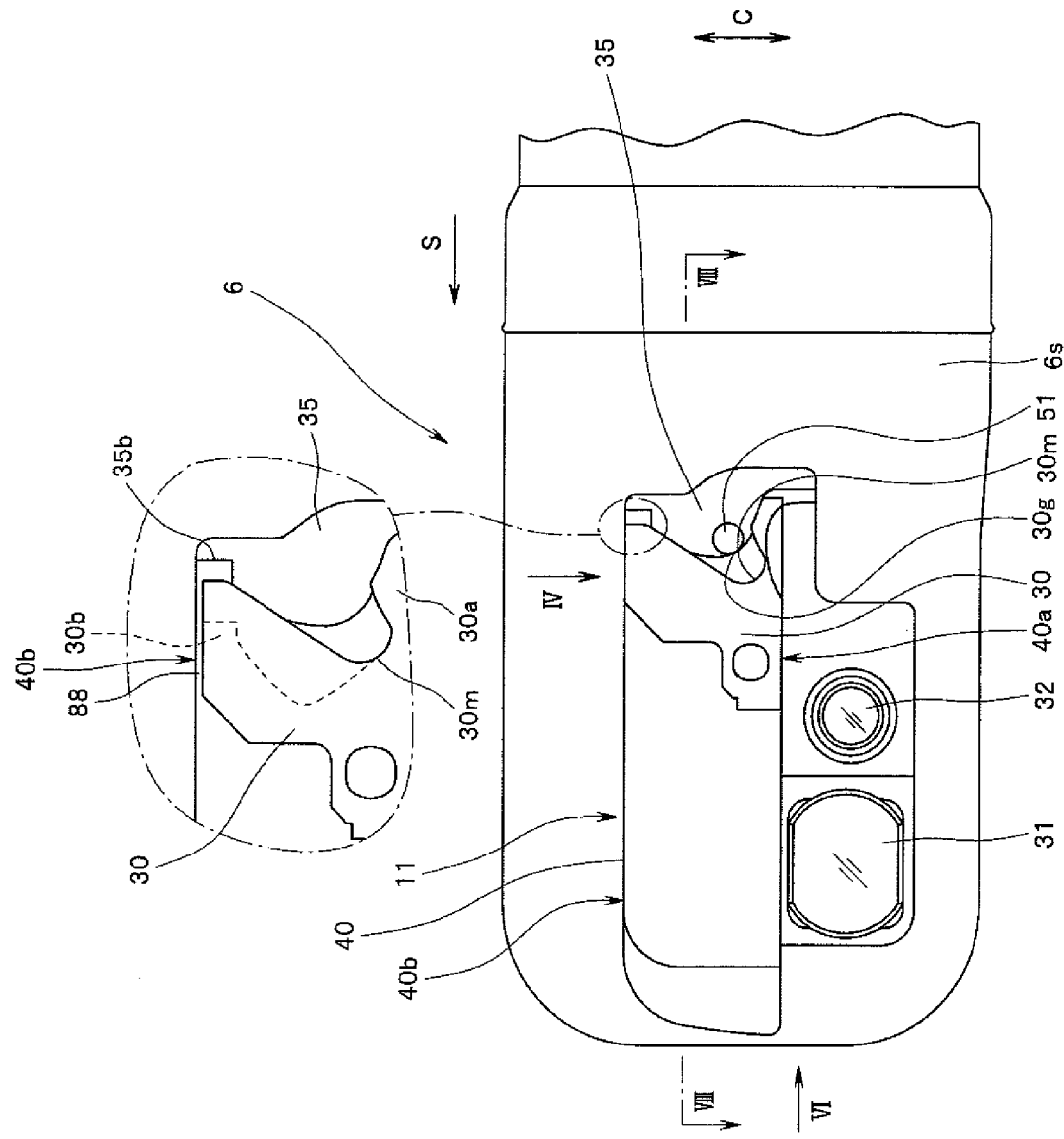
FIG. 9 is a partial enlarged plan view schematically showing a state in which the treatment instrument elevator base provided in the distal end opening of FIG. 2 is raised to raise the treatment instrument.
Figure 10:
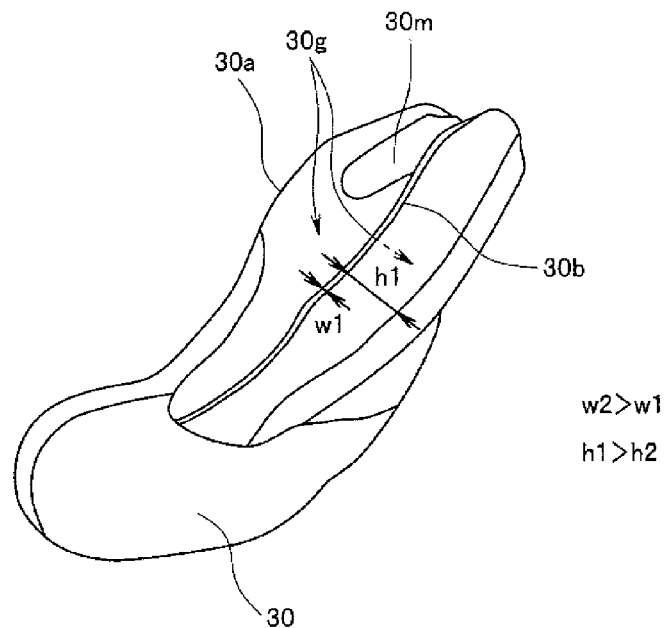
FIG. 10 is a perspective view showing a shape of the treatment instrument elevator base in FIG. 3.

Furthermore, FIG. 9 is a partial enlarged plan view schematically showing a state in which the treatment instrument elevator base provided in the distal end opening of FIG. 2 is raised to raise the treatment instrument. FIG. 10 is a perspective view showing a shape of the treatment instrument elevator base in FIG. 3.

Figure 11:
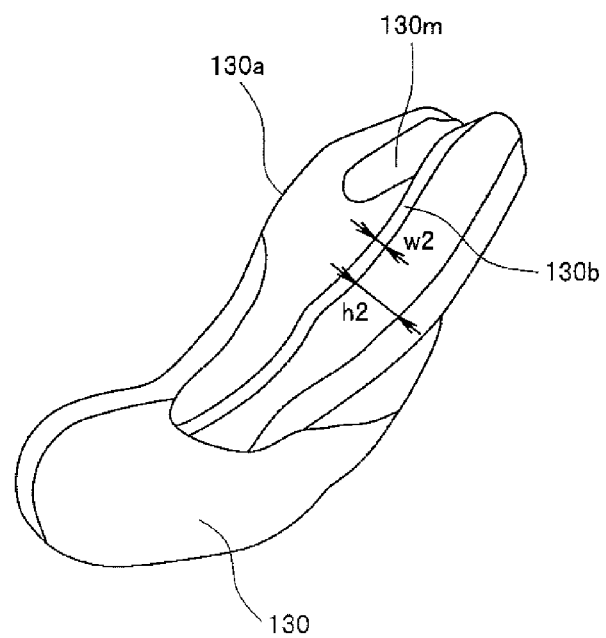
FIG. 11 is a perspective view showing a shape of a conventional treatment instrument elevator base.
Figure 12:
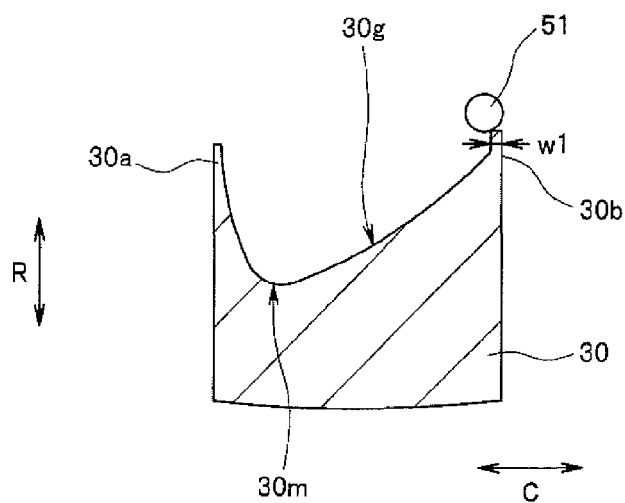
FIG. 12 is a diagram schematically showing a cross section of the treatment instrument elevator base in FIG. 10.
Figure 13:
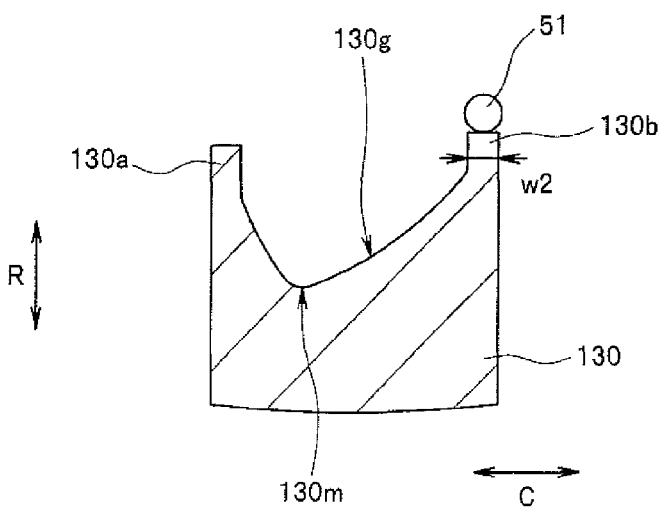
FIG. 13 is a diagram schematically showing a cross section of the treatment instrument elevator base of FIG. 11.

Further, FIG. 11 is a perspective view showing a shape of a conventional treatment instrument elevator base. FIG. 12 is a diagram schematically showing a cross section of the treatment instrument elevator base in FIG. 10. FIG. 13 is a diagram schematically showing a cross section of the treatment instrument elevator base of FIG. 11.

Figure 14:
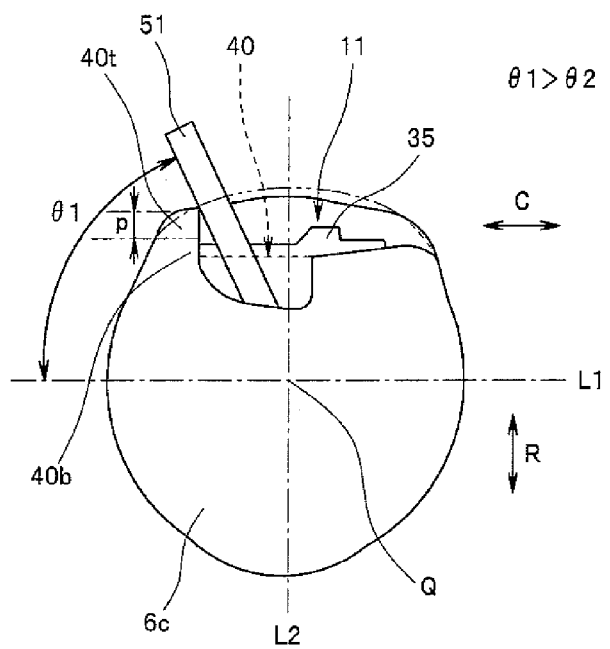
FIG. 14 is a diagram of a state where in a distal end opening of a distal end portion, a treatment instrument protrudes on a tilt toward a side spaced apart from an observation optical system, as viewed from a IX direction in FIG. 2.
Figure 15:
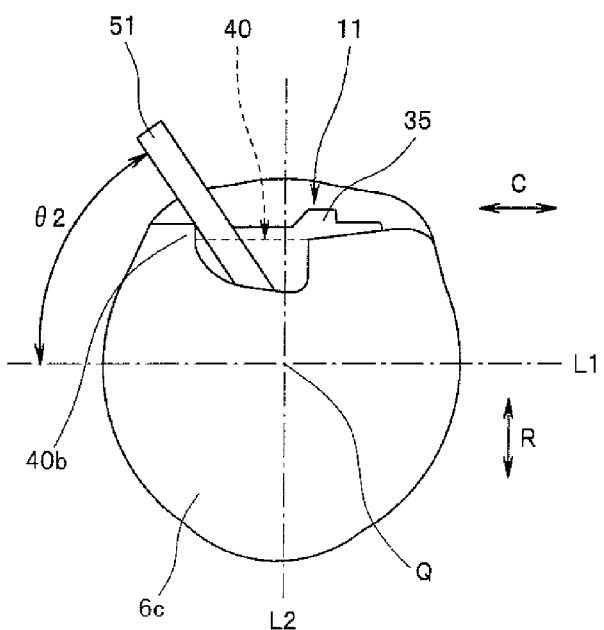
FIG. 15 is a diagram showing a state where in a distal end opening of a conventional distal end portion, a treatment instrument protrudes on a tilt toward a side spaced apart from an observation optical system.
Figure 16:
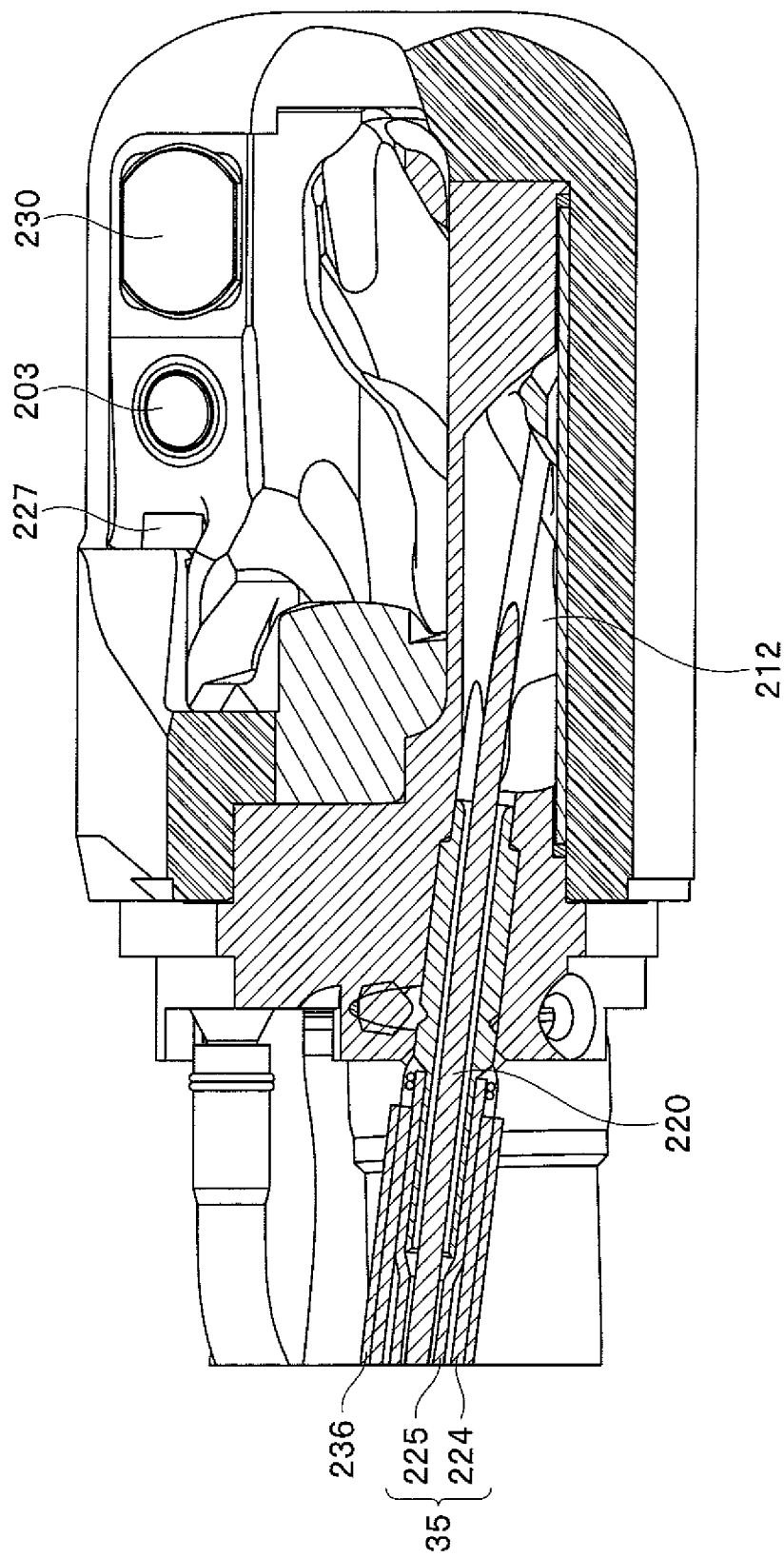
FIG. 16 is a diagram showing a partial cross section of a distal end side of an insertion portion of an endoscope shown in supplementary notes.
Figure 17:
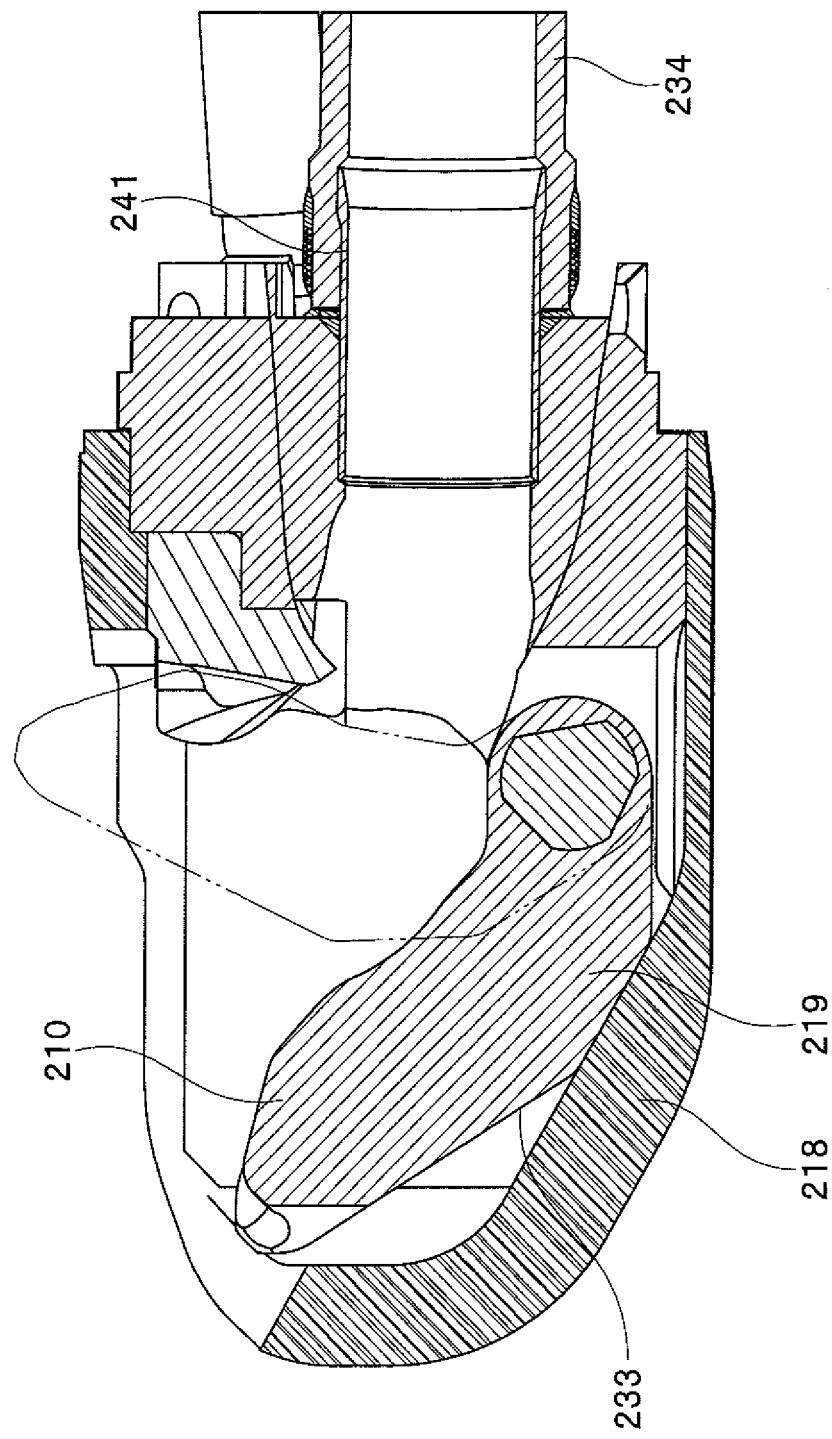
FIG. 17 is a cross-sectional view of a position including a treatment instrument elevator base at the distal end side of the insertion portion in FIG. 16 along an insertion axis direction.
Figure 18:
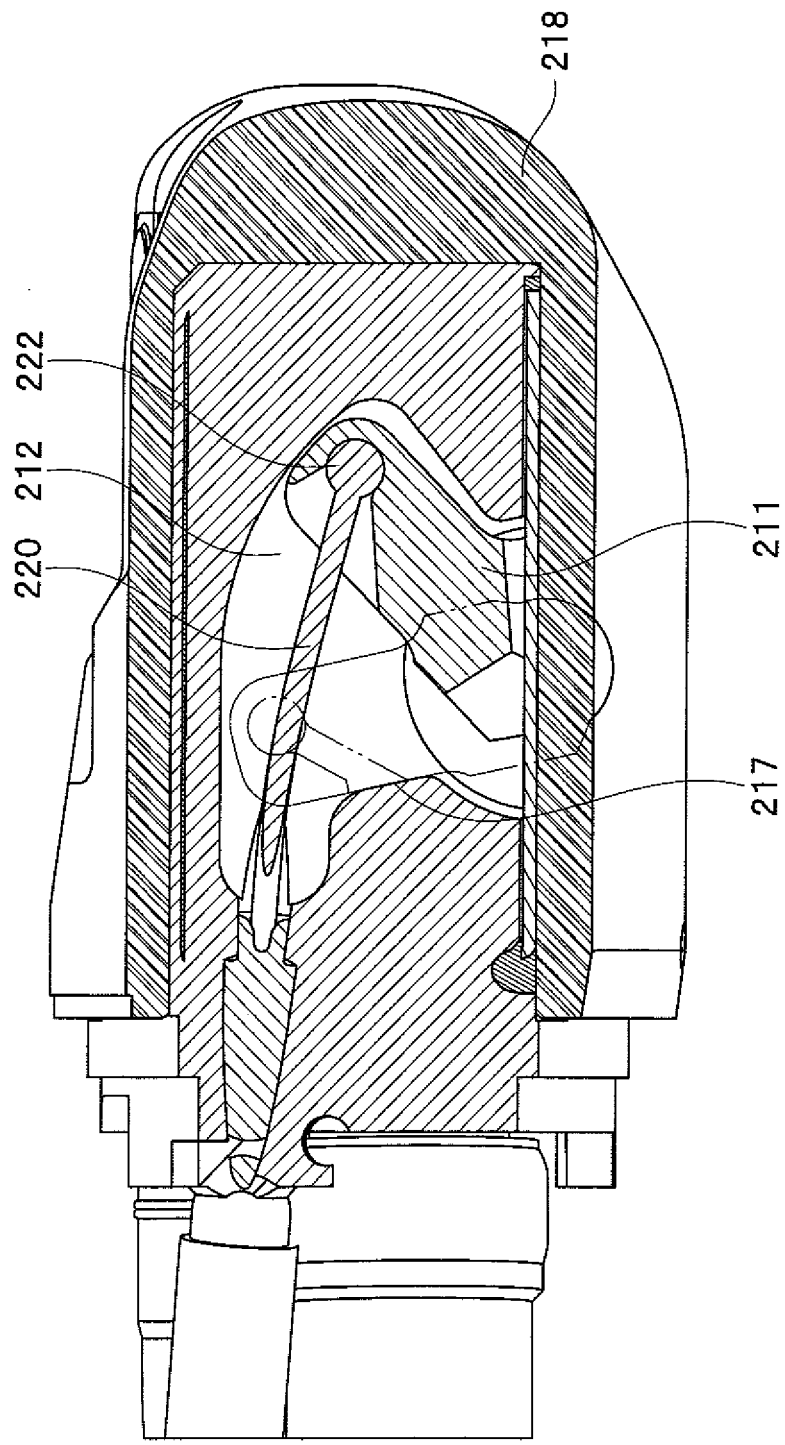
FIG. 18 is a cross-sectional view of a position including an accommodation chamber at a distal end side of an insertion portion in FIG. 15 along an insertion axis direction.
Figure 19:
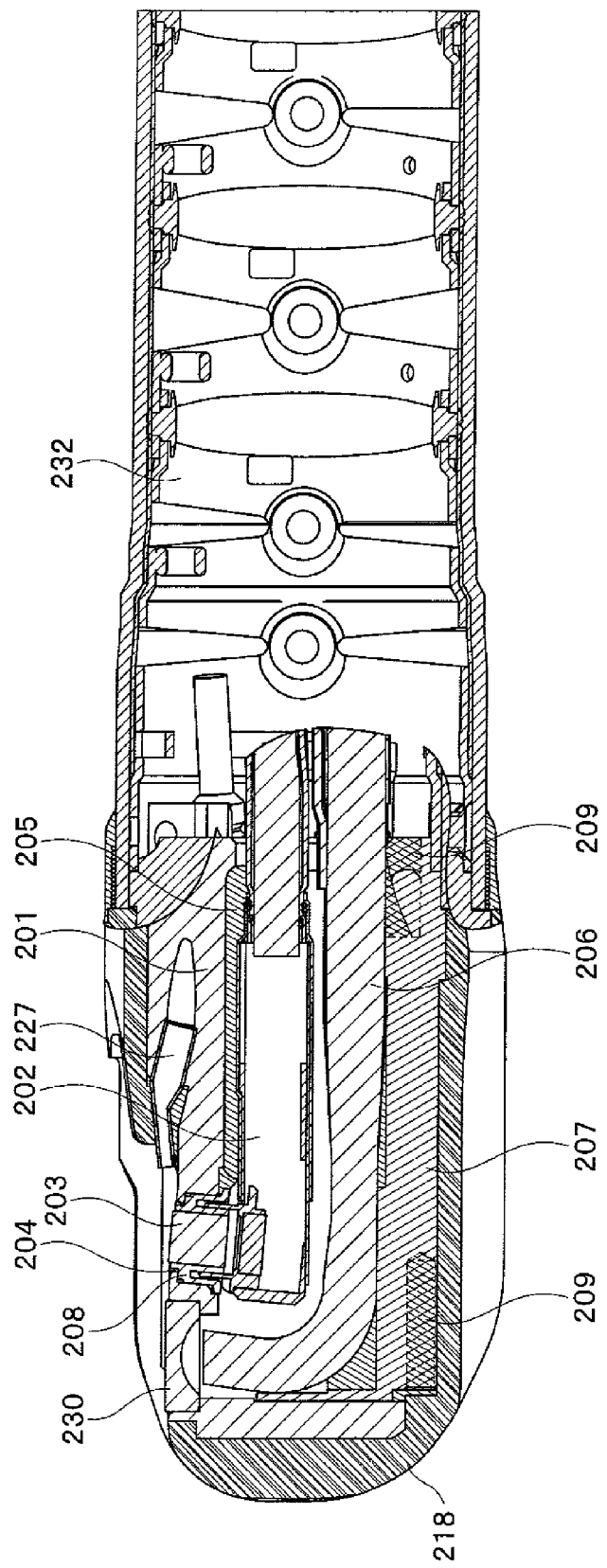
FIG. 19 is a cross-sectional view showing the distal end side of the insertion portion in FIG. 16 as well as a bending portion, along the insertion axis direction.
Figure 20:
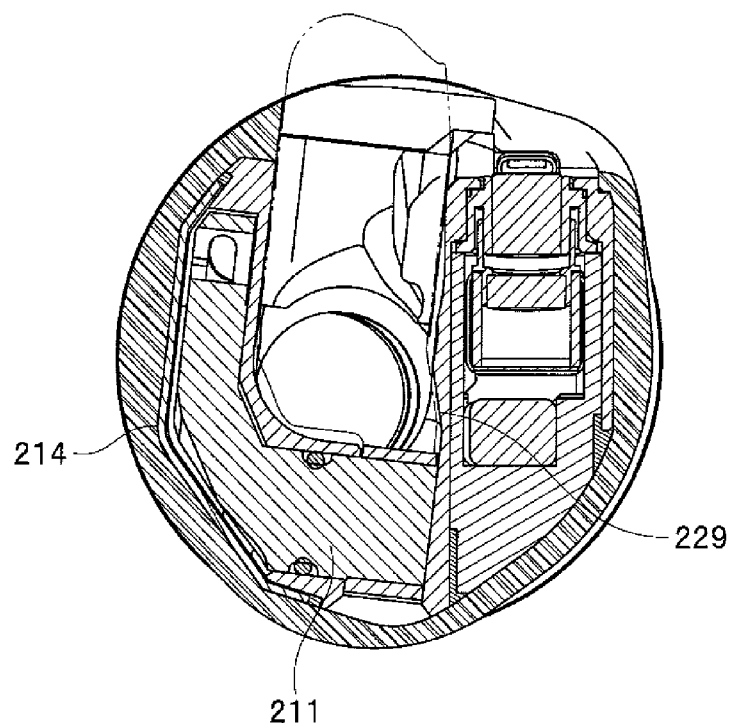
FIG. 20 is a cross-sectional view of a position including a driving arm in FIG. 18, taken in a direction orthogonal to the insertion axis direction.
Figure 21:
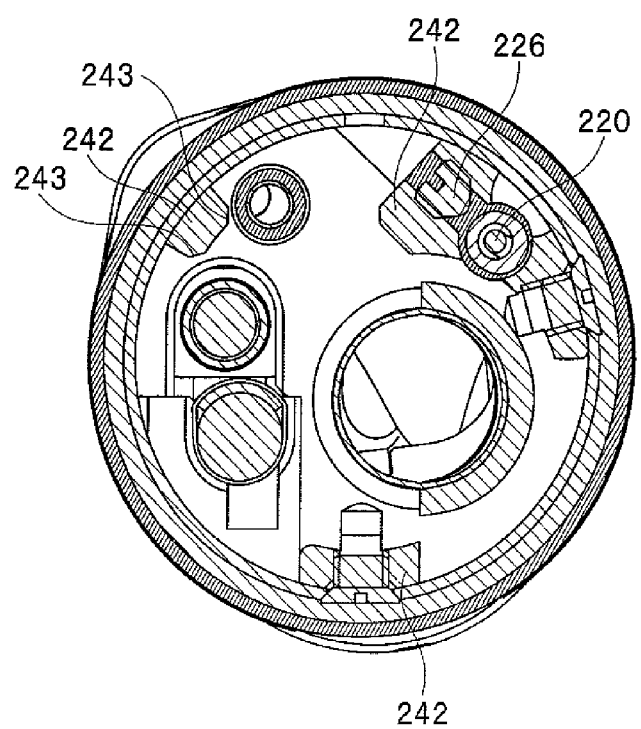
FIG. 21 is a cross-sectional view of a distal end portion of the insertion portion in FIG. 19, taken in a direction orthogonal to the insertion axis direction.
Figure 22:
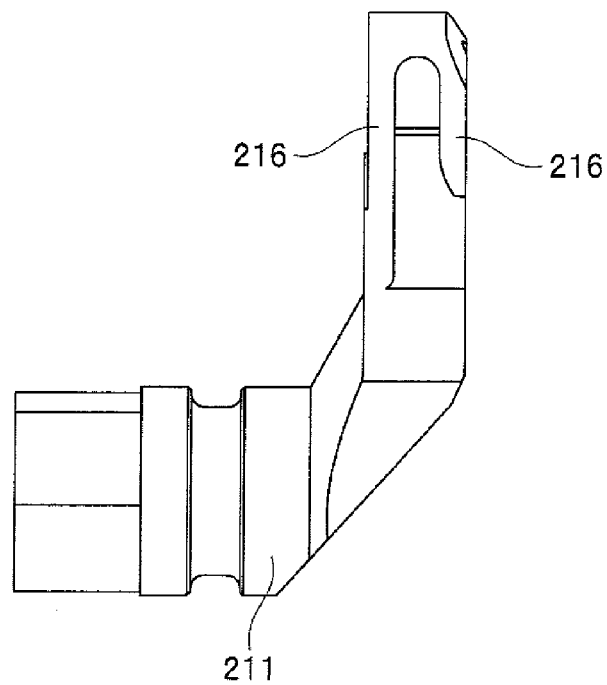
FIG. 22 is an enlarged view showing the driving arm in FIG. 18.
Figure 23:
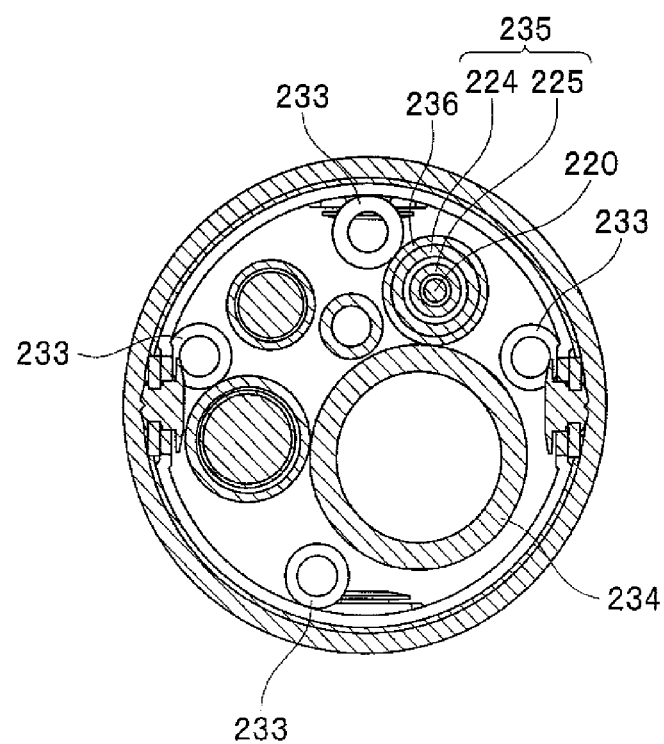
FIG. 23 is a cross-sectional view of the bending portion of the insertion portion in FIG. 19, taken in the direction orthogonal to the insertion axis direction.

Furthermore, FIG. 14 is a diagram of a state where in a distal end opening of a distal end portion, a treatment instrument protrudes on a tilt toward a side spaced apart from an observation optical system, as viewed from a IX direction in FIG. 2. FIG. 15 is a diagram showing a state where in a distal end opening of a conventional distal end portion, a treatment instrument protrudes on a tilt toward a side spaced apart from an observation optical system.

As shown in FIG. 1, an endoscope apparatus 100 is composed of an endoscope 1 and a peripheral device 10. A main part of the endoscope 1 is composed of an insertion portion 2 inserted into a subject, an operation portion 3, and a universal cord 5.

The peripheral device 10 includes a light source apparatus 21, a video processor 22, a connection cable 23 that electrically connects the light source apparatus 21 with the video processor 22, and a monitor 25 that are placed on a rack 26. Further, the endoscope 1 and the peripheral device 10 having such configurations are connected with each other via a connector 19.

The connector 19 is connected with the light source apparatus 21 of the peripheral device 10. The connector 19 is provided with a pipe sleeve, not shown, connected with an end of a conduit 91 (see FIG. 7) constituting a treatment instrument insertion channel 41 described later (see FIG. 7) and a light guide pipe sleeve, not shown, constituting an end of a light guide, and an electrical contact portion and the like.

The light guide is led through the universal cord 5, the operation portion 3 and the insertion portion 2, to a distal end portion 6 described later of the insertion portion 2. The light guide sends illumination light from the light source apparatus 21 to an illumination lens 31 (see FIG. 2) described later of the distal end portion 6, and expands the light to illuminate an inside of a body cavity.

The operation portion 3 of the endoscope 1 is provided with a bending operation knob 3a, an air and water supply operation button 3b, a suction operation button 3c, a treatment instrument elevator base operation knob 3d for performing an operation to raise a treatment instrument elevator base 30 (see FIG. 2) described later, and a treatment instrument insertion port 3e through which a treatment instrument is inserted into the conduit 91 provided in the insertion portion 2 of the endoscope 1.

The insertion portion 2 of the endoscope 1 is composed of the distal end portion 6 at a distal end side of the insertion portion 2, a bending portion 7, and a flexible tube portion 8. The bending portion 7 is bent with the bending operation knob 3a provided on the operation portion 3, and is provided between the distal end portion 6 and the flexible tube portion 8.

As shown in FIGS. 7 and 8, the distal end portion 6 includes a distal end portion main body 6s having a main part composed of a distal end rigid portion 6h made of, for example, metal and a distal end cover 6c formed of a non-conductive member such as resin so as to surround the distal end rigid portion 6h. The distal end cover 6c is fixed to the distal end rigid portion 6h with an adhesive or the like.

A long hole 6ha is formed in the distal end rigid portion 6h along an insertion direction S. In addition, an accommodation chamber 40s is made at a distal end side of the long hole 6ha, and the treatment instrument elevator base 30 described later is provided in the accommodation chamber 40s.

Further, a connection pipe 90 is fitted at a proximal end side of the long hole 6ha as a guide path for treatment instruments or a guide wire 50 (see FIG. 3). Furthermore, a distal end side of a conduit 91 as a guide path for the treatment instruments or the guide wire 50 is fixed to a circumference of a proximal end side of the connection pipe 90. A passage of the long hole 6ha, the connection pipe 90, and the conduit 91 composes a treatment instrument insertion channel 41 in the present embodiment.

Further, the guide wire 50 is usually made with an elastic force by coating a core wire made of, for example, a superelastic alloy with a flexible shell resin (heat-shrinkable tube type) such as Teflon (registered trademark), urethane, or the like. Recently, Teflon-coated guide wires have been known.

When a treatment instrument such as forceps and a catheter is selectively inserted into an extremely thin duct such as a pancreatic duct, a bile duct, or a hepatic duct using the endoscope 1, a catheter is inserted into the treatment instrument insertion channel of the endoscope, and a distal end portion of the catheter is inserted into the foregoing duct by raising the treatment instrument elevator base 30 as described later.

Next, a guide wire is inserted through a pipe sleeve at a proximal end side of the catheter, and in radioscopy, it is confirmed that the guide wire 50 is correctly inserted into the duct. Then, the catheter is withdrawn with the guide wire 50 remained in the duct, and when a next treatment instrument is inserted into the duct, the treatment instrument is guided. As a result, exchangeability of treatment instruments is improved.

Now, as shown in FIGS. 1 to 3, FIG. 7, and FIG. 8, a cutout portion 11 made by cutting out an outer circumferential face side is formed on an outer circumferential face being a side surface of the distal end portion main body 6s. On the outer circumferential face of the cutout portion 11, a distal end opening 40 being an opening at the distal end side of the treatment instrument insertion channel 41 and having, for example, a substantially rectangular planar shape is provided. That is, the distal end opening 40 is an opening of the accommodation chamber 40s.

Further, as shown in FIGS. 2 and 3, on an outer circumferential face of the cutout portion 11, along a direction C orthogonal to an insertion direction S, an observation optical system 32 of an image pickup unit being not shown and embedded in the distal end portion 6 and an illumination lens 31 of an illumination optical system are provided along with the distal end opening 40.

Further, in the distal end portion 6, in a position facing the distal end opening 40 in the treatment instrument insertion channel 41, specifically, in the accommodation chamber 40s, the treatment instrument elevator base 30 is provided to lead a treatment instrument protruding from the distal end opening 40 through the treatment instrument insertion channel 41, to a desired position by raising the treatment instrument.

That is, the treatment instrument elevator base 30 is raised to change an advancing direction of a treatment instrument inserted from the treatment instrument insertion port 3e into the treatment instrument insertion channel 41, from an advancing direction along the insertion direction S in the treatment instrument insertion channel 41 to the direction of the distal end opening 40.

As shown in FIGS. 7 and 8, the treatment instrument elevator base 30 is substantially triangle in cross section, and one end of the treatment instrument elevator base 30 is pivotally attached to an elevator base swivel pivot point 30j at a lower side of the accommodation chamber 40s provided in the distal end rigid portion 6h, so that the other end side of the treatment instrument elevator base 30 swivels in the accommodation chamber 40s. A position at which a driving arm (described later) coupled to the treatment instrument elevator base 30 contacts the distal end rigid portion 6h is a maximum raised position of the treatment instrument elevator base 30.

The treatment instrument elevator base 30 is connected with one end of a raising wire, not shown, the other end of which is connected with an elevator base driving mechanism, not shown, provided in the operation portion 3. The raising wire is inserted through the insertion portion 2.

The treatment instrument elevator base 30 is raised about the elevator base swivel pivot point 30j from a lowered state shown in FIGS. 2, 5, and 7, into a state shown in FIGS. 3, 4, 6, and 8 through the elevator base driving mechanism and the raising wire by a treatment instrument elevator base operation knob 3d being operated, or conversely, the treatment instrument elevator base 30 is lowered from a raised state.

In addition, as shown in FIGS. 2, 7, and 8, a surface of the treatment instrument elevator base 30 opposite to the distal end opening 40 constitutes a guide plane 30g that leads a treatment instrument to the distal end opening 40. At a position close to the other end part of the treatment instrument elevator base 30, a groove 30m being substantially V-shaped or U-shaped in cross section is formed at a substantially central position of the guide plane 30g in the direction C.

The groove 30m is used in the above-described center lock in which the guide wire 50 protruding from the distal end opening 40 is releasably engaged between the treatment instrument elevator base 30 and an insulating member 35 described later when the treatment instrument elevator base 30 is maximum raised. In addition, the groove 30m holds a treatment instrument on the guide plane 30g when a protruding direction of the treatment instrument from the distal end opening 40 is changed as the treatment instrument elevator base 30 is raised and lowered.

Further, as shown in FIGS. 2 and 3, on both end portions of the guide plane 30g in the direction C, edges 30a and 30b are respectively formed along the insertion direction S.

As shown in FIG. 10, since heights h1 of side walls constituting the edges 30a and 30b are greater than heights h2 of side walls constituting edges 130a and 130b of a treatment instrument elevator base having a conventional engage groove 130m shown in FIG. 11 (h1>h2), the side walls are steeply formed so that a wall thickness w1 of the edges 30a and 30b is thinner than a wall thickness w2 of the conventional edges 130a and 130b (w1<w2).

It should be noted that, as shown in FIG. 13, the wall thickness w2 of the conventional edges 130a and 130b is a thickness that causes the treatment instrument 51 to be mounted on the edge 130a or 130b when the treatment instrument elevator base 30 is raised with the treatment instrument 51 contacting the edge 130a or the edge 130b.

Further, the wall thickness w1 of the edges 30a and 30b in the present embodiment is a thickness in which when the treatment instrument elevator base 30 is raised with a tubular treatment instrument 51 contacting the edge 30a or the edge 30b, as shown in FIG. 12, the treatment instrument 51 does not mount on the edge 30a or the edge 30b, and the treatment instrument 51 easily slips off, that is, the treatment instrument 51 easily falls onto a guide plane 30g side.

As shown in FIGS. 2 to 8, the insulating member 35 is provided on a surface facing the distal end opening 40 of the distal end rigid portion 6h, namely, a wall portion at a proximal end side of the distal end opening 40. It should be noted that in the present embodiment, the insulating member 35 constitutes a second wall portion of the distal end opening 40.

Further, as shown in FIGS. 2 and 3, in an extending direction of the insulating member 35, namely, the direction C, grooves 35a and 35b being run off portions for the edges 30a and 30b are formed on an end portion at an observation optical system 32 side described later and an end portion at a side spaced apart from the observation optical system 32, respectively. When the treatment instrument elevator base is maximum raised as shown in FIGS. 3, 4, 6, and 8, the edges 30a and 30b of the treatment instrument elevator base 30 are fitted in the grooves 35a and 35b, respectively.

It should be noted that with respect to the insulating member 35, the proximal end side of the direction C and the insertion direction S of the groove 35a is larger than the groove 35b. It is because the groove 35a is used in the side lock described above.

The edge 30a constitutes a contact portion that contacts the guide wire 50 as the treatment instrument elevator base 30 is raised when in the distal end opening 40, the side lock described above is performed with the guide wire 50 tilted toward the observation optical system 32 side with respect to the direction C.

Thus, after the treatment instrument elevator base 30 is maximum raised, by the guide wire contacting a surface of the edge 30a and a surface constituting the groove 35a of the insulating member 35, the guide wire 50 is retained between the edge 30a and the groove 35a, and thereby a position of the guide wire 50 is fixed.

That is, the guide wire 50 is fixed by the edge 30a of the treatment instrument elevator base 30, at a corner between a wall portion 40a, which is a wall of a first wall portion along the insertion direction S of the distal end opening 40 and close to the observation optical system 32, and the end portion of the insulating member 35 at the observation optical system 32 side in the direction C.

As shown in FIG. 3, the edge 30b constitutes a contact portion that contacts the guide wire 50 as the treatment instrument elevator base 30 is raised when in the distal end opening 40, the guide wire 50 is fixed with the guide wire 50 tilted toward the side spaced apart from the observation optical system 32 with respect to the direction C.

Thus, as shown with a circle of a dash-dot line in FIG. 3, after the treatment instrument elevator base 30 is maximum raised, by the guide wire 50 contacting a surface of the edge 30b, a surface constituting the groove 35b of the insulating member 35, and of the first wall portion along the insertion direction S of the distal end opening 40, the surface of the wall portion 40b spaced apart from the observation optical system 32 in the direction C, the guide wire 50 is retained by the three points of the edge 30b, the groove 35b, and the wall portion 40b, and thereby a position of the guide wire 50 is fixed.

That is, the guide wire 50 is fixed by the edge 30b of the treatment instrument elevator base 30, at a corner between the wall portion 40b and the end portion of the insulating member 35 at the side spaced apart from the observation optical system 32 in the direction C.

It should be noted that as shown with the circle of the dash-dot line in FIG. 3, a width t3 of the edge 30b in the direction C is smaller than a diameter t1 of the guide wire 50 (t3<t1).

It is because if the width t3 is greater than the diameter t1, when in the distal end opening 40, the guide wire 50 is raised by raising the treatment instrument elevator base 30 in a lowered state with the guide wire 50 tilted toward the side spaced apart from the observation optical system 32, the guide wire 50, which contacts the edge 30b with the raise, easily moves to the groove 30m side in the direction C, and thereby the guide wire 50 is not enabled to be fixed by the edge 30b, the groove 35b, and the wall portion 40b after the guide wire 50 is maximum raised.

Further, since the width t3 is smaller than the diameter t1, a part of the guide wire 50 is easily allowed to go into a gap 88 described later between the edge 30b and the wall portion 40b.

In addition, as shown with the circle of the dash-dot line in FIG. 3, the gap 88 with the width t2 is formed in the direction C between the edge 30b of the treatment instrument elevator base 30 and the wall portion 40b.

In the distal end opening 40, when the guide wire 50 is raised by raising the treatment instrument elevator base 30 in the lowered state with the guide wire 50 tilted toward the side spaced apart from the observation optical system 32, a part of the guide wire 50 that contacts the edge 30b goes into the gap 88.

As a result, as the treatment instrument elevator base 30 is raised and a part of the guide wire 50 goes into the gap 88, the guide wire 50 is raised with the part in the gap 88 contacting the wall portion 40b.

Therefore, since the guide wire 50 does not move to the groove 30m side in the direction C as the treatment instrument elevator base 30 is raised, after the treatment instrument elevator base 30 is maximum raised, the guide wire 50 reliably contacts the three points of the groove 35b, the edge 30b, and the wall portion 40b and is fixed.

It should be noted that the width t2 of the gap 88 is smaller than the diameter t1 of the guide wire 50 (t2<t1). It is because if the width t2 is greater than the diameter t1, as the treatment instrument elevator base 30 is raised, the entire of the guide wire 50 goes into the gap between the edge 30b and the first wall portion 40b, and thereby the guide wire 50 cannot be raised, so that the guide wire 50 is not enabled to be fixed.

Further, as shown in FIGS. 4, 6, and 8, when the treatment instrument elevator base 30 is maximum raised to fix the guide wire 50, the other end side portion of the treatment instrument elevator base 30 extends out the insertion portion 2 from the distal end opening 40 outward in a radial direction R by a height h.

It is because if the other end side portion of the treatment instrument elevator base 30 is lower than the distal end opening 40 in the radial direction R when the treatment instrument elevator base 30 is maximum raised, that is, the other end side portion is in the accommodation chamber 40s, when the guide wire 50 is raised by raising the treatment instrument elevator base 30, the guide wire 50 may move to the groove 30m side in the direction C due to elastic force of the guide wire 50.

Thus, in the present embodiment, when the guide wire 50 is fixed with the guide wire 50 tilted in the direction C toward the side spaced apart from the observation optical system 32 in the distal end opening 40, the treatment instrument elevator base 30 is maximum raised, and thereby the guide wire 50 contacts a surface of the edge 30b of the treatment instrument elevator base 30, a surface of the wall portion 40b, and a surface constituting the groove 35b of the insulating member 35 to be releasably engaged.

According to this, unlike the case of the above-described side lock configuration involving the groove 35a, a large groove such as the groove 35a may not be formed in the insulating member 35. Therefore, machining the groove 35b is easy as well as the guide wire 50 can be fixed in a reduced space.

In addition, in the case of the side lock configuration, the guide wire 50 is fixed by two surfaces of a surface of the edge 30a and a surface constituting the groove 35a, but in the present fixation configuration, the guide wire 50 is fixed by three surfaces of a surface of the edge 30b of the treatment instrument elevator base 30, a surface of the wall portion 40b, and a surface constituting the groove 35b of the insulating member 35, so that a position of the guide wire 50 can be more reliably fixed.

Thus, the endoscope 1 can be provided in which the guide wire 50 can be reliably fixed in a reduced space in the distal end opening 40.

Further, of the wall portions 40a and 40b along the insertion direction S and formed on the distal end rigid portion 6h by the distal end opening 40, as shown in FIG. 14, in the opening direction of the distal end opening 40, namely, in the direction R orthogonal to the insertion direction S and the direction C, the wall portion 40b at the side spaced apart from the observation optical system 32 is higher than by p than a conventional height of the wall portion 40b as shown in FIG. 15.

That is, a height of the distal end cover 6c of a portion constituting the wall portion 40b is higher than a conventional height of a portion of the wall portion 40b by p in the direction R. The same goes for the case where only the distal end rigid portion 6h without the distal end cover 6c constitutes the distal end portion 6. In this case, it is only necessary for a height of a portion constituting the wall portion 40b of the distal end rigid portion 6h to be higher than a conventional height of a portion of the wall portion 40b by p in the direction R.

Now, a specific configuration will be described in which the wall portion 40b of the present embodiment is higher than a conventional height of the wall portion 40b by p in the direction R. As shown in FIG. 15, as viewed from the distal end side in the insertion direction S, the conventional distal end portion 6 was substantially circle. A height of the wall portion 40b also contributed to the circle form.

However, in the configuration of the present embodiment, as shown in FIG. 14, the wall portion 40b has a protruding portion 40t that protrudes by p in the height direction R as compared to the conventional wall portion 40b.

Specifically, before the treatment instrument elevator base 30 is raised, when the treatment instrument 51 protrudes from the distal end opening 40 on a tilt toward the wall portion 40b side, as shown in FIG. 15, assuming that in the conventional wall portion 40b, an angle formed by a line L1 along the direction C and passing a center Q of the distal end portion 6 and a line L2 along the direction R and passing the center Q is 90°, as well as an angle formed by the treatment instrument 51 extending out from the distal end opening 40 and contacting the wall portion 40b and the line L1 is θ2, in the present embodiment, as shown in FIG. 14, since the wall portion 40b protrudes in the direction R by p as compared with the conventional wall portion 40b due to the protruding portion 40t, an angle formed by the treatment instrument 51 extending out from the distal end opening 40 and contacting the protruding portion 40t of the wall portion 40b and the line L1 is θ1 being greater than θ2 (θ1>θ2).

As a result, because of the protruding portion 40t, the treatment instrument 51 is inclined, namely, raised toward a line L2 side parallel to the direction R as compared with the conventional case, so that the treatment instrument 51 will be readily led to the guide plane 30g.

As shown in FIG. 15, before the treatment instrument elevator base 30 is raised, when the treatment instrument 51 protrudes from the distal end opening 40 on a tilt toward the wall portion 40b side, if the treatment instrument 51 is lowered to the line L1 side, it takes time to raise the treatment instrument 51 toward the line L2 side, namely, the guide plane 30g side, so that just before the treatment instrument elevator base is maximum raised, the treatment instrument 51 may fall to the guide plane 30g.

However, as shown in FIG. 14, when the treatment instrument 51 protrudes from the distal end opening 40 on a tilt toward the wall portion 40*b* side, if the treatment instrument 51 is raised to the line L2 side due to the protruding portion 40*t*, the treatment instrument 51 can fall to the line L2 side, that is, the treatment instrument 51 can fall to the guide plane 30*g* earlier than the case of FIG. 15 as the treatment instrument elevator base 30 is raised.

Therefore, if the problem of an outside diameter of the distal end portion 6 being increased is ignored, the greater the protruded height p of the protruding portion 40*t* is, the more quickly the treatment instrument 51 can fall to the guide plane 30*g*. However, actually, in order not for the outside diameter of the distal end portion 6 to become excessively large, the height p of the protruding portion 40*t* is set to an optimum position.

Thus, in the present embodiment, the edge 30*b* of the treatment instrument elevator base 30 is steeply formed to be thinner than the conventional edge 30*b* (w1<w2), as well as the wall portion 40*b* of the distal end opening 40 is formed to be higher than the conventional wall portion 40*b* by p.

It should be noted that a modification will be described below.

The present embodiment has described the fixation configuration for the guide wire 50 fixed with the guide wire 50 tilted in the direction C toward the side spaced apart from the observation optical system 32 in the distal end opening 40.

The embodiment is not limited to the configuration, and may also be applied to the side lock configuration in which the guide wire 50 is fixed with the guide wire 50 tilted in the direction C toward the observation optical system 32 side in the distal end opening 40.

That is, with respect to the insulating member 35, by making the grooves 35*a* and 35*b* the same size, the guide wire 50 may be fixed by three surfaces of a surface of the edge 30*a* of the treatment instrument elevator base 30, a surface of the wall portion 40*a*, and a surface constituting the groove 35*a*.

In this case, it is needless to say that a width of the edge 30*a* in the direction C is smaller than the diameter t1 of the guide wire 50 and a width of the gap between the edge 30*a* and the wall portion 40*a* in the direction C is also smaller than the diameter t1 of the guide wire 50.

Further, the present embodiment has described that the grooves 35*a* and 35*b* are formed in the insulating member 35, but the embodiment is not limited thereto. If the run off portions for the edges 30*a* and 30*b* of the treatment instrument elevator base 30 are not necessary to be provided in the insulating member 35, the groove 35*a* and 35*b* may not be formed.

Therefore, in this case, if the guide wire 50 is fixed with the guide wire 50 tilted in the direction C toward the side spaced apart from the observation optical system 32 in the distal end opening 40, after the treatment instrument elevator base 30 is maximum raised, a position of the guide wire 50 is fixed by contacting the surface of the edge 30*b* of the treatment instrument elevator base 30, the surface of the wall portion 40*b*, and the surface of the portion of the insulating member 35 spaced apart in the direction C from the observation optical system 32.

In addition, the present embodiment has described that the insulating member 35 is provided on the wall portion at the proximal end side of the distal end opening 40, and the second wall portion is constituted on the insulating member 35, but the embodiment is not limited thereto. The wall portion itself at the proximal end side of the distal end opening 40 may constitute the second wall portion.

Therefore, in this case, if the guide wire 50 is fixed with the guide wire 50 tilted toward the side spaced apart from the observation optical system 32 in the distal end opening 40, after the treatment instrument elevator base 30 is maximum raised, a position of the guide wire 50 is fixed by contacting the surface of the edge 30*b* of the treatment instrument elevator base 30, the surface of the wall portion 40*b*, the surface of the portion of the wall portion at the proximal end side of the distal end opening 40, the portion being spaced apart in the direction C from the observation optical system 32.

Figure 24:
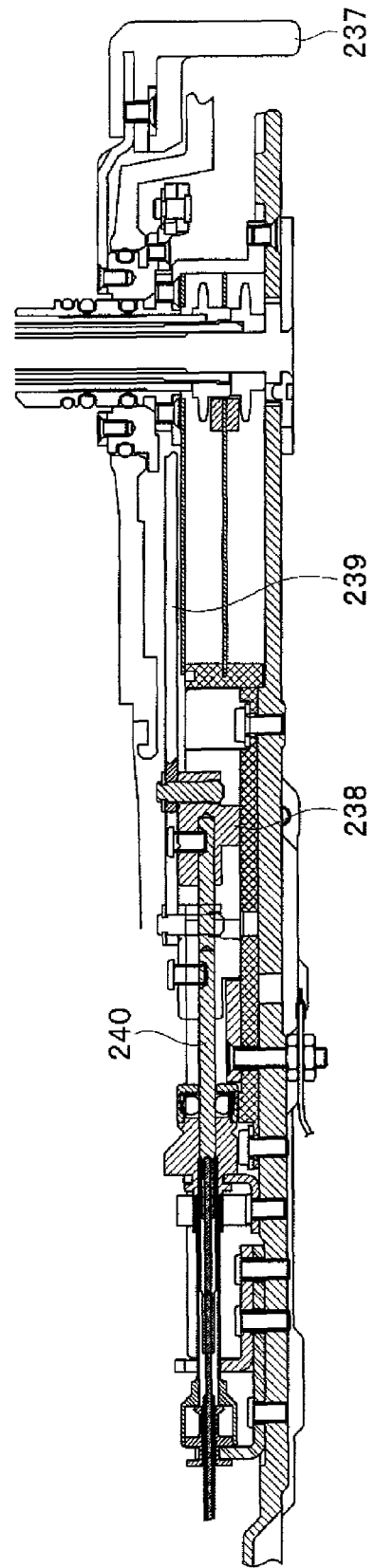
FIG. 24 is a partial cross-sectional view showing a configuration of a hand-side operation portion of an endoscope in FIG. 15.

In the foregoing endoscope, without limiting to the configuration described above, the following problems, configurations adopted to solve the problems, and effects resulting from the configurations can be considered. In this respect, description will be made based on a configuration of a distal end portion of an endoscope shown in FIG. 16 through FIG. 23 and a configuration in a hand-side operation portion of the endoscope shown in FIG. 24.

(1) A configuration is desired which can improve assembling of a distal end portion main body 201 and an image pickup unit 202 and allow exchanging the image pickup unit 202 easily. In other words, a configuration is desired which can improve workability of assembling the image pickup unit 202 to the distal end portion main body 201 and then applying an adhesive to a part between an objective lens 203 and the distal end portion main body 201 and allow the image pickup unit 202 to be easily replaced.

To achieve the configuration, when the image pickup unit 202 is fixed to the distal end portion main body 201, an epoxy system adhesive 204 is used for the vicinity of a lens frame 208 and a silicon system adhesive 205 is used for the other areas.

Further, a light guide fiber 206 is fixed to a light guide cover 207 with the epoxy system adhesive 204 as a unit. With a flange provided on the light guide cover 207, the image pickup unit 202 is pressed against the distal end portion main body 201 and the light guide cover 207 is fixed to the distal end portion main body 201 with the epoxy system adhesive 204.

Further, when the light guide fiber 206 is positioned to the light guide cover 207, the light guide fiber 206 is directly brought into contact with the light guide cover 207.

A procedure to remove the image pickup unit 202 is as follows: removing a unit of the light guide cover 207 and the light guide fiber 206 from the distal end portion main body 201, and pushing a lens frame 208 from an exposed first objective lens surface side.

Thus, by minimizing an amount of usage of the epoxy system adhesive 204, which has strong adhesive force, and using the silicon system adhesive 205 for the other parts, the image pickup unit 202 can easily be removed. Further, since the light guide cover 207 fixes two components of the light guide fiber 206 and the image pickup unit 202, the number of components can be reduced.

(2) In the conventional configurations, when the unit of the light guide cover 207 and the light guide fiber 206 is removed, it is difficult to easily remove the unit without scattering fibers of the light guide fiber 206.

To solve the problem, both sides of the light guide cover 207 have been provided with apertures 209 into which a jig is put. Owing to such a configuration, when the light guide cover 207 is removed from the distal end portion main body 201, the light guide cover 207 can easily be removed by putting a jig into the aperture 209 in the light guide cover 207.

(3) To attain waterproofness of an accommodation chamber 212 in which a driving arm 211 coupled with a treatment instrument elevator base 210 and driving the treatment instrument elevator base 210 is accommodated, conventionally, a minute screw has been used to position and fix a cap member 214 to the distal end portion main body 201.

However, in the conventional configurations, the number of components increases and fine assembling work has been needed to be learned. To solve the problem, a convex portion to be fitted in the distal end portion main body 201 has been provided in the cap member 214 side.

In such a configuration, a positioning portion (convex portion) is integrally provided on the cap member 214, a concave portion in which the positioning portion is fitted is provided in the distal end portion main body 201, the cap member 214 and the distal end portion main body 201 are assembled so that the positioning portion is fitted in the concave portion, and an adhesive is applied to a gap between the cap member 214 and the distal end portion main body 201. As a result, without increasing the number of components, the cap member 214 can be positioned to the distal end portion main body 201 and fixed to acquire waterproofness.

(4) To treat a disorder of a pancreaticobiliary duct system or the like, a thick treatment instrument, a diameter of which is similar to a diameter of a channel 234, is used. Because the treatment instrument is thick and hard, the strength of the driving arm 211 is required to raise the treatment instrument. If the size of the driving arm 211 is increased to obtain the strength, a distal end outside diameter is increased. Thus, thick portions 216 of the driving arm 211 are made asymmetric, and thereby the strength of the driving arm 211 can be improved without increasing a distal end portion outside diameter of the endoscope.

(5) In the conventional configurations, the foregoing driving arm 211 is under a heavy load, and there has been an object to improve an ability of the driving arm 211 to withstand a load produced by being repeatedly used. To achieve the object, a raised side of the treatment instrument elevator base 210 has been configured so that the driving arm 211 is brought into contact with the distal end portion main body 201.

Thereby, even if a treatment instrument raising wire 220 is pulled after the elevator base is maximum raised, since the driving arm 211 is contacting the distal end portion main body 201 by surface, the driving arm 211 will not be under more load, a load such as a shake and a twist is not generated on the driving arm 211.

On the other hand, a lowered side of the treatment instrument elevator base 210 is configured so that the treatment instrument elevator base 210 is brought into contact with the distal end portion main body 201 or a distal end portion cover 218. In such a configuration, similarly, a reaction force of the treatment instrument allows the driving arm 211 not to contact the distal end portion main body 201 when the elevator base is maximum lowered, so that a load onto the driving arm 211 is reduced and deformation and a failure of the driving arm 211 can be prevented from occurring.

(6) Further, since the raised side of the treatment instrument elevator base 210 is configured so that the driving arm 211 is brought into contact with the distal end portion main body 201, there is constantly a gap between the treatment instrument elevator base 210 and the distal end portion main body 201, and an antiseptic liquid flows reliably, so that the cleaning/sterilization property of the endoscope is improved.

(7) When the treatment instrument elevator base 210 is assembled to the driving arm 211, since fitting portions of the treatment instrument elevator base 210 and the driving arm 211 are not cylindrical, the positioning of the both is necessary. However, since the distal end portion main body 201 is between the both during assembling the same, the assembling has to be carried out blindly.

Thus, a configuration is adopted which allows easy assembling by providing the treatment instrument elevator base 210 with at least one convex portion, bringing the convex portion and an assembling jig into contact, and inserting the driving arm 211 into the treatment instrument elevator base 210 at a predetermined angle.

In such a configuration, the assembling is easy since the positioning can be spontaneously achieved by bringing the convex portion of the treatment instrument elevator base 210 and the assembling jig into contact. Additionally, because the convex portion is on only a required part of the treatment instrument elevator base 210, the shape is simple and the cleaning property is improved.

(8) There has been an object to improve an ability of the treatment instrument raising wire 220 to withstand the repeated sliding by the driving arm 211 and the treatment instrument raising wire 220 coupled with the driving arm 211.

To achieve the object, only an area in which the driving arm 211 contacts the treatment instrument raising wire 220 has been chamfered or rounded. Thereby, the treatment instrument raising wire 220 can be prevented from snapping, and the object can be achieved inexpensively because only a necessary part is chamfered or rounded.

(9) Further, the treatment instrument raising wire 220 may rub against the distal end portion main body 201 to cause the wire to snap or an abnormal feel to be produced. To solve the problem, a pipe sleeve distal end at a distal end side of a forceps raising conduit 235 has been widely rounded.

In such a configuration, since a part contacting the treatment instrument raising wire 220 is not an edge, an abnormal feel is less produced when a treatment instrument raising lever 237 is operated.

(10) A wire anchorage 222 is joined to a distal end of the treatment instrument raising wire 220 by brazing, and the wire anchorage 222 is coupled with the driving arm 211. Since the wire anchorage 222 is a minute component, there has been an object to improve brazing workability.

To achieve the object, of the wire anchorage 222, only a side into which solder runs has been chamfered. In such a configuration, because melted solder broadens toward the end, the solder less protrudes from an end face of a treatment instrument raising wire fixing member 240. In addition, a post-process becomes unnecessary.

(11) Unlike a front-view type endoscope, a side-view type endoscope is complex in configuration because the treatment instrument elevator base 210 is provided therein.

Therefore, there has been an object to improve the cleaning property. To achieve the object, so as not to affect a function of the treatment instrument elevator base 210, a back face 223 of the treatment instrument elevator base 210 has been shaved to broaden a space with respect to the distal end cover. In such a configuration, a cleaning liquid and an antiseptic liquid become easy to flow. In addition, since it is easy to insert a brush, the cleaning/sterilization property is improved.

(12) In the conventional configurations, because a coil 224 or a tube 225 of the forceps raising conduit 235 is adhered to the distal end portion main body 201, if the coil 224 or the tube 225 of the forceps raising conduit 235 needs repair because of pitch displacement and the like, repair is troublesome.

To solve the problem, the forceps raising conduit 235 has been detachably provided with respect to the distal end portion main body 201. A screw 226 fixing the forceps raising conduit 235 to distal end portion main body 201 is positioned at an operation portion side as compared with an end of the distal end portion cover 218.

In such a configuration, the forceps raising conduit 235 can easily be replaced without breaking the distal end portion cover 218. Further, the forceps raising conduit 235 can be replaced in a ropeway manner.

That is to say, a maximum outside diameter of components composing the forceps raising conduit 235 is determined so as not to interfere with other internal components in the insertion portion. In such a configuration, because it is not necessary to extract all the internal components from the insertion portion and only the forceps raising conduit 235 can be extracted and re-assembled, required man-hours for repair can be reduced.

(13) In the conventional configurations, there has been an object to prevent an air and water supply nozzle 227 from falling off without increasing a distal end outside diameter.

To achieve the object, the distal end portion cover 218 has been allowed to prevent the air and water supply nozzle 227 from coming off. In such a configuration, since a screw or the like for fixing the air and water supply nozzle 227 is not necessary, the distal end outside diameter can be maintained and the number of components can be reduced.

(14) In the conventional configurations, there has been an object to achieve maximum possible shortness of the distal end rigid portion while the driving arm 211 is made thick for strength without impairing an insertion property of a treatment instrument.

To achieve the object, a shape of the distal end portion main body 201 has been formed to overlap a treatment instrument guide plane so as to avoid an interference with a treatment instrument. In such a configuration, the distal end rigid portion is made short without impairing the insertion property of a treatment instrument, and thereby the operativity in the duodenum can be improved.

(15) In the conventional configurations, there has been an object to keep the strength of and reduce the size of a fitting portion of the driving arm 211 and the treatment instrument elevator base 210.

To achieve the object, the fitting portion of the driving arm 211 and the treatment instrument elevator base 210 has been carved an object side. In addition, a ball end mill has been used for a cutter to carve.

In such a configuration, the strength of the driving arm 211 can be kept, the size of the distal end portion outside diameter can be reduced, and a ball end mill processing achieves a shape that less collects filth.

(16) In the conventional configurations, there has been a problem that Molykote® paste is adhered to a back face of a light guide lens 230 and endoscope image becomes darker.

To solve the problem, on an end face of the distal end portion main body 201, a quick-drying filling agent is filled between the image pickup unit 202 and the light guide fiber 206.

In such a configuration, an amount of outgoing light beam can be kept by easy operations.

(17) In the conventional configurations, by the raising operation of the elevator base in a bended state and repeated bending, the coil 224 or the tube 225 guiding the treatment instrument raising wire 220 causes pressure, and a bending operation wire receiver 233 of a bending duct 232 causes the channel 234 to be crushed, resulting in a low insertion property of treatment instruments.

To solve the problem, a clearance between the bending operation wire receiver 233 at a down side of a bending direction and the channel 234 has been acquired. (i.e., an assembling angle of the bending wire receiver is changed).

In such a configuration, the crush of the channel 234 caused by the bending operation wire receiver 233 at the bending direction down side and the channel 234 contacting each other can be prevented from occurring.

(18) In the conventional configurations, by the raising operation of the elevator base in a bended state and repeated bending, the coil 224 or the tube 225 guiding the treatment instrument raising wire 220 causes pressure, and the bending operation wire receiver 233 causes the channel 234 to be crushed, resulting in a low insertion property of treatment instruments.

To solve the problem, the radius R has been more rounded, and thereby a load onto the channel 234 has been reduced. In such a configuration, the crush of the channel 234 can be prevented from occurring.

(19) In the conventional configurations, by the raising operation of the elevator base in a bended state and repeated bending, the coil 224 or the tube 225 guiding the treatment instrument raising wire 220 causes pressure, and the bending operation wire receiver 233 causes the channel 234 to be crushed, resulting in a low insertion property of treatment instruments.

To solve the problem, in order to reduce the pressure from the forceps raising conduit 235, an outside diameter of the forceps raising conduit 235 has been reduced to form a clearance. In such a configuration, the crush of the channel 234 can be prevented from occurring.

(20) In the conventional configurations, there has been a problem that if the distal end portion is angled, the coil 224 or the tube 225 composing the forceps raising conduit 235 receives pressure which is suddenly released like a spring and the movement is transferred. Consequently, movements of an angle knob and the distal end are not in synchronization, and disadvantageously, a distal end of a scope moves swiftly.

To solve the problem, to control the movement of the coil 224 or the tube 225 composing the forceps raising conduit 235 (to move smoothly) when the distal end portion is angled, the coil 224 or the tube 225 has been coated with a heat-shrinkable tube 236.

In such a configuration, the movements of the coil 224 or the tube 225 with the angling operations can be smoothened. The heat-shrinkable tube 236 may be used for only around a bending portion with a high load or may also be used for a total length of the insertion portion.

(21) Furthermore, the coil 224 or the tube 225 composing the forceps raising conduit 235 is coated with the heat-shrinkable tube 236 with the pitches broadened in advance, and then the broadened pitches are opened. Thereby, the heat-shrinkable tube 236 extends throughout the pitches as if the pitches were stuck to each other.

In such a configuration, a pitch displacement of the coil 224 or the tube 225 can be prevented from occurring as well as a small stroke of the treatment instrument raising lever 237 can be enough to operate the treatment instrument elevator base 210.

(22) In the conventional configurations, by the raising operation of the elevator base in a bended state and repeated bending, the coil 224 or the tube 225 guiding the treatment instrument raising wire 220 causes pressure, and the bending operation wire receiver 233 causes the channel 234 to be crushed, resulting in a low insertion property of treatment instruments.

To solve the problem, an extending direction of the forceps raising conduit 235 is made substantially parallel to a longitudinal axis of the endoscope, instead of being bended, and a clearance between the channel 234 and the forceps raising conduit 235 is achieved to reduce the load onto the channel 234.

In such a configuration, the crush of the channel 234 can be prevented from occurring. Further, an abnormal feel can be prevented from occurring when the treatment instrument raising lever 237 acts.

(23) In the conventional configurations, when the treatment instrument raising lever 237 is operated, the driving arm 211 is inclined by weight of a treatment instrument or the like, and the driving arm 211 rubs against a wall of the distal end portion main body 201, so that there has been the case in which an abnormal feel is received from the treatment instrument raising lever 237.

To solve the problem, the extending direction of the forceps raising conduit 235 is made substantially parallel to the longitudinal axis of the endoscope, and the driving arm 211 is operated substantially parallel to a wall of the distal end portion main body 201 between the driving arm 211 of the distal end portion main body 201 and the treatment instrument elevator base 210.

Further, ridgelines of the distal end portion main body 201 and the sliding driving arm 211 are chamfered to allow smooth operations. In such a configuration, an abnormal feel can be prevented from occurring when the treatment instrument raising lever 237 is operated.

(24) In the conventional configurations, there has been a case in which an abnormal feel is received when a forceps raising lever is operated.

To solve the problem, a clearance between a link member 239 and a coupling member 238 has been reduced in order for the forceps raising lever in the operation portion and the coupling member 238 coupling the treatment instrument raising wire 220 with a metal member by soldering to move back and forth smoothly.

In such a configuration, an abnormal feel can be prevented from occurring when the treatment instrument raising lever 237 is operated.

(25) In the conventional configurations, because loads concentrate upon a coupling member 238 and a treatment instrument raising wire fixing member 240 (in the operation portion) coupling the treatment instrument raising wire 220, the treatment instrument raising wire fixing member 240 may be broken with the smaller number of uses than conventional products.

To solve the problem, the strength of the treatment instrument raising wire fixing member 240 (in the operation portion) will be improved as well as at first, the treatment instrument raising wire fixing member 240 (in the operation portion) has been thickened so that the treatment instrument raising wire fixing member 240 is strong enough not to be broken.

In such a configuration, both safety and durability can be improved.

(26) In the conventional configurations, if a distal end configuration portion is tried to be short in order to improve operators' operativity, because a protruded length of the channel connection pipe 241 from the distal end portion main body 201 is short, binding the channel 234 is challenging.

To solve the problem, a protruded portion 242 of the distal end portion main body 201, the portion being contacted by a thread for binding, has been chamfered to enable the thread to less snap. In such a configuration, the assembling workability is improved.

What is claimed is:

1. An endoscope comprising: a distal end opening of a treatment instrument insertion channel provided in an insertion portion inserted into a subject, the opening being made at a side surface of a distal end portion at a distal end side of an insertion direction of the insertion portion; a treatment instrument elevator base that is, in the distal end portion, provided at a position facing the distal end opening in the treatment instrument insertion channel and leads a distal end of a treatment instrument protruding from the distal end opening, to a desired position; a first wall portion along the insertion direction of the distal end opening; and a second wall portion at a proximal end side of the insertion direction of the distal end opening and provided with a groove in which a part of the treatment instrument elevator base is fitted when the treatment instrument elevator base is raised, wherein the groove is formed to the second wall portion at a corner between a proximal end in the insertion direction of the first wall portion and an end portion of the second wall portion which is continuous to the proximal end, and wherein as the treatment instrument elevator base is raised, a guide wire opening is releasably engaged by in a state of being in contact with three parts including the treatment instrument elevator base, the first wall portion, and the second wall portion, with a part of the guide wire protruded from the distal end opening being fallen to the groove.

2. The endoscope according to claim 1, wherein as the treatment instrument elevator base is raised, a width of an engagement portion of the treatment instrument elevator base is smaller than a diameter of the guide wire, and the engagement portion engages the guide wire.

3. The endoscope according to claim 2, wherein the engagement portion of the treatment instrument elevator base is an edge along the insertion direction of the treatment instrument elevator base.

4. The endoscope according to claim 1, wherein a width of a gap between the treatment instrument elevator base and the first wall portion is smaller than the diameter of the guide wire.

5. The endoscope according to claim 1, wherein when a position of the guide wire is fixed as the treatment instrument elevator base is raised, a part of the treatment instrument elevator base extends out the insertion portion from the distal end opening outward in a radial direction.

6. The endoscope according to claim 1, wherein the second wall portion is in an insulating member provided at a position facing the distal end opening of the distal end portion.

7. The endoscope according to claim 1, wherein
an observation optical system to observe the subject portion is provided along with the distal end opening, on the side surface of the distal end portion in an extending direction of the second wall portion, and
a position of the guide wire is fixed by contacting the treatment instrument elevator base, the first wall portion spaced apart from the observation optical system in the extending direction of the second wall portion, and the second wall portion.

* * * * *